(12) United States Patent
DiRocco et al.

(10) Patent No.: US 9,808,461 B2
(45) Date of Patent: Nov. 7, 2017

(54) PROTECTION OF RENAL TISSUES FROM ISCHEMIA THROUGH INHIBITION OF THE PROLIFERATIVE KINASES CDK4 AND CDK6

(75) Inventors: Derek P. DiRocco, Brookline, MA (US); Norman E. Sharpless, Chapel Hill, NC (US); Jay C. Strum, Hillsborough, NC (US); John E. Bisi, Apex, NC (US); Patrick J. Roberts, Durham, NC (US); Benjamin D. Humphreys, Brookline, MA (US); Kwok-Kin Wong, Arlington, MA (US)

(73) Assignees: The University of North Carolina at Chapel Hill, Chapel Hill, NC (US); G1 Therapeutics, Chapel Hill, NC (US); Brigham and Women's Hospital, Boston, MA (US)

( * ) Notice: Subject to any disclaimer, the term of this patent is extended or adjusted under 35 U.S.C. 154(b) by 992 days.

(21) Appl. No.: 13/988,158

(22) PCT Filed: Nov. 17, 2011

(86) PCT No.: PCT/US2011/061202
§ 371 (c)(1),
(2), (4) Date: Jul. 31, 2013

(87) PCT Pub. No.: WO2012/068381
PCT Pub. Date: May 24, 2012

(65) Prior Publication Data
US 2013/0303543 A1 Nov. 14, 2013

Related U.S. Application Data

(60) Provisional application No. 61/458,140, filed on Nov. 17, 2010.

(51) Int. Cl.
| | | |
|---|---|---|
| A61K 31/497 | (2006.01) | |
| A61K 31/519 | (2006.01) | |
| A61K 31/192 | (2006.01) | |
| A61K 31/436 | (2006.01) | |
| A61K 31/616 | (2006.01) | |
| A61K 38/13 | (2006.01) | |
| A61K 31/505 | (2006.01) | |

(52) U.S. Cl.
CPC .......... *A61K 31/519* (2013.01); *A61K 31/192* (2013.01); *A61K 31/436* (2013.01); *A61K 31/616* (2013.01); *A61K 38/13* (2013.01); *A61K 31/505* (2013.01)

(58) Field of Classification Search
CPC .............. A61K 31/505; A61K 31/519
USPC .................................................. 514/252.16
See application file for complete search history.

(56) References Cited

U.S. PATENT DOCUMENTS

| | | |
|---|---|---|
| 5,591,855 A | 1/1997 | Hudkins et al. |
| 5,628,984 A | 5/1997 | Boucher, Jr. |
| 5,739,110 A | 4/1998 | Bogden et al. |
| 6,291,504 B1 | 9/2001 | Nugiel et al. |
| 6,369,086 B1 | 4/2002 | Davis et al. |
| 6,521,759 B2 * | 2/2003 | Kim ..................... C07D 231/12 548/184 |
| 6,610,684 B2 | 8/2003 | Zaharevitz et al. |
| 6,667,346 B2 | 12/2003 | Reddy et al. |
| 6,936,612 B2 | 8/2005 | Barvian et al. |
| 6,982,277 B2 | 1/2006 | Gudkov et al. |
| 7,208,489 B2 | 4/2007 | Barvian et al. |
| 7,345,171 B2 | 3/2008 | Beylin et al. |
| 8,598,186 B2 | 12/2013 | Tavares et al. |
| 8,598,197 B2 | 12/2013 | Tavares et al. |
| 9,616,062 B2 | 4/2017 | Sharpless et al. |
| 2002/0042412 A1 | 4/2002 | Zaharevitz et al. |
| 2003/0069430 A1 | 4/2003 | Davis et al. |
| 2003/0073668 A1 | 4/2003 | Booth et al. |
| 2003/0229026 A1 | 12/2003 | Al-Awar et al. |
| 2004/0006074 A1 | 1/2004 | Kelley et al. |
| 2004/0048915 A1 | 3/2004 | Engler et al. |
| 2005/0222163 A1 | 10/2005 | Eck et al. |
| 2007/0027147 A1 | 2/2007 | Hayama et al. |
| 2007/0179118 A1 | 8/2007 | Barvian et al. |
| 2007/0270362 A1 | 11/2007 | Harlan et al. |
| 2008/0085890 A1 | 4/2008 | Tsou et al. |
| 2008/0161355 A1 | 7/2008 | Curry et al. |

(Continued)

FOREIGN PATENT DOCUMENTS

| | | |
|---|---|---|
| CA | 2656290 | 1/2008 |
| CN | 1278794 | 1/2001 |

(Continued)

OTHER PUBLICATIONS

Baughn et al., "A Novel Orally Active Small Molecule Potently Induces G1 Arrest in Primary Myeloma Cells and Prevents Tumor Growth by Specific Inhibition of Cyclin-Dependent Kinase 4/6," Cancer Research. vol. 66 No. 15 pp. 7661-7667 (2006).
Bernhard et al., "Reducing the radiation-induced $G_2$ delay causes HeLa cells to undergo apoptosis instead of mitotic death," Int. J. Radiat. Biol. vol. 69, No. 5 pp. 575-584 (1996).
Blagosklonny et al., "Exploiting Cancer Cell Cycling for Selective Protection of Normal Cells," Cancer Research. vol. 61 pp. 4301-4305 (2001).
Bucher, N., and Britten, C.D., "G2 checkpoint abrogation and checkpoint kinase-I targeting in the treatment of cancer," British Journal of Cancer. vol. 98 pp. 523-528 (2008).
Burdelya et al., "An Agonist of Toll-Like Receptor 5 Has Radioprotective Activity in Mouse and Primate Models," Science. vol. 320 pp. 226-230 (2008).

(Continued)

*Primary Examiner* — Kevin E Weddington
(74) *Attorney, Agent, or Firm* — Jenkins, Wilson, Taylor & Hunt, P.A.

(57) ABSTRACT

The presently disclosed subject matter relates to methods and compositions for protecting cells and or tissues from damage due to ischemia. In particular, the presently disclosed subject matter relates to the protective action of cyclin dependent kinase 4/6 (CDK4/6) inhibitors administered to subjects that have been exposed to, or that are at risk of, ischemia.

21 Claims, 6 Drawing Sheets

(56) References Cited

U.S. PATENT DOCUMENTS

| | | |
|---|---|---|
| 2008/0182853 A1 | 7/2008 | Kruman et al. |
| 2011/0224221 A1 | 9/2011 | Sharpless et al. |
| 2011/0224227 A1 | 9/2011 | Sharpless et al. |
| 2012/0100100 A1 | 4/2012 | Sharpless et al. |
| 2014/0227222 A1 | 8/2014 | Sharpless et al. |
| 2015/0111896 A1 | 4/2015 | Sharpless et al. |

FOREIGN PATENT DOCUMENTS

| | | | |
|---|---|---|---|
| CN | 1379668 | 11/2002 | |
| EP | 2429566 | 3/2012 | |
| JP | 2001-517652 | 10/2001 | |
| JP | 2005-519909 | 7/2005 | |
| JP | 2005-526920 | 9/2005 | |
| JP | 2007-530425 | 11/2007 | |
| JP | 2007-530654 | 11/2007 | |
| WO | WO98/33798 | 8/1998 | |
| WO | WO99/15500 | 4/1999 | |
| WO | WO01/12188 | 2/2001 | |
| WO | WO02/44174 | 6/2002 | |
| WO | WO03/062236 | 7/2003 | |
| WO | WO03/100147 | 12/2003 | |
| WO | WO 2004/065378 A1 | 8/2004 | |
| WO | WO2005/005426 | 1/2005 | |
| WO | WO2005/094830 | 10/2005 | |
| WO | WO 2006002119 A2 * | 1/2006 | ............ A61K 31/00 |
| WO | WO2006/074985 | 7/2006 | |
| WO | WO2007/140222 A2 | 12/2007 | |
| WO | WO2008/005538 | 1/2008 | |
| WO | WO 2008/076946 | 6/2008 | |
| WO | WO2008/079933 | 7/2008 | |
| WO | WO2009/061345 | 5/2009 | |
| WO | WO2009/085185 A1 | 7/2009 | |
| WO | WO 2010/020675 | 2/2010 | |
| WO | WO2010/039997 | 4/2010 | |
| WO | WO2010/051127 | 5/2010 | |
| WO | WO2010/132725 | 11/2010 | |
| WO | WO2012/061156 | 5/2012 | |
| WO | WO2012/068381 | 5/2012 | |

OTHER PUBLICATIONS

Chu et al., "Discovery of [4-Amino-2-(1-methanesulfonylpiperidin-4-ylamino)pyrimidin-5-yl](2,3-difluoro-6-methoxyphenyl)methanone (R547), a Potent and Selective Cyclin-Dependent Kinase Inhibitor with Significant in Vivo Antitumor Activity," J. Med. Chem. vol. 49 pp. 6549-6560 (2006).

Davis et al., "Genistein Induces Radioprotection by Hematopoietic Stemm Cell Quiescence," International Journal of Radiation Biology. vol. 84, No. 9 pp. 713-726 (2008).

Davis et al., "Retraction," Science. vol. 298, p. 2327 (2002).

Dickson, M.A., and Schwartz, G.K., "Development of cell-cycle inhibitors for cancer therapy," Current Oncology. vol. 16, No. 2 pp. 36-43 (2009).

Dickson et al. "Phase II Trial of the CDK4 Inhibitor PD0332991 in Patients with Advanced CDK4-Amplified Well-Differentiated or Dedifferentiated Liposarcoma," Journal of Clinical Oncology. vol. 31, No. 16 pp. 2024-2028 (2013).

El-Deiry, "Meeting Report: The International Conference on Tumor Progression and Therapeutic Resistance," Cancer Research. vol. 65, No. 11 pp. 4475-4484 (2005).

Extended European Search Report corresponding to European Patent Application No. 09 818 530.9-1216 dated Sep. 24, 2012.

Extended European Search Report corresponding to European Patent Application No. 09 823 989.0-2123 dated May 11, 2012.

Extended European Search Report corresponding to European Patent Application No. 10 775 575.3-1456 dated Aug. 5, 2013.

Finn et al., "PD 0332991, a selective cyclin D kinase 4/6 inhibitor, preferentially inhibits proliferation of luminal estrogen receptor-positive human breast cancer cell lines in vitro," Breast Cancer Research. vol. 11, No. 5 p. R77 (2009).

Fry et al., "Specific inhibition of cyclin-dependent kinase 4/6 by PD 0332991 and associated antitumor activity in human tumor xenografts," Molecular Cancer Therapeutics. vol. 3, No. 11 pp. 1427-1437 (2004).

Guo et al., "Staurosporine modulates radiosensitivity and radiation-induced apoptosis in U937 cells," Int. J. Radiat. Biol. vol. 82, No. 2 pp. 97-109 (2006).

Hallahan et al., "Inhibition of Protein Kinases Sensitizes Human Tumor Cells to Ionizing Radiation," Radiation Research. vol. 129 pp. 345-350 (1992).

Hérodin et al., "Short-term injection of antiapoptotic cytokine combinations soon after lethal γ-irradiation promotes survival," Blood. vol. 101 pp. 2609-2616 (2003).

Hershman et al., "Acute Myeloid Leukemia or Myelodysplastic Syndrome Following Use of Granulocyte Colony-Stimulating Factors During Breast Cancer Adjuvant Chemotherapy," J. Natl. Cancer Inst. vol. 99, No. 3 pp. 196-205 (2007).

Hirose et al., "Abrogation of the Chk1-mediated G2 Checkpoint Pathway Potentiates Temozolomide-induced Toxicity in a p53-independent Manner in Human Glioblastoma Cells", Cancer Research. vol. 61 pp. 5843-5849.(2001).

Johnson et al., "Mitigation of Hematologic Radiation Toxicity in Mice Through Pharmacological Quiescence Induced by CDK4/6 Inhibition," J. Clin. Investigation. vol. 120 pp. 2528-2536 (2010).

Karaman et al., "A quantitative analysis of kinase inhibitor selectivity," Nature Biotechnology. vol. 26, No. 1 pp. 127-132 (2008).

Keyomarsi, K., and Pardee, A.B., "Selective protection of normal proliferating cells against the toxic effects of chemotherapeutic agents," Progress in Cell Cycle Research. vol. 5 pp. 527-532 (2003).

Kim et al., "Enhancement of Radiation Effects of Flavopiridol in Uterine Cervix Cancer Cells," Cancer Research Treatment. vol. 37, No. 3 pp. 191-195 (2005).

Knockaert et al., "Pharmacological inhibitors of cyclin-dependent kinases," Trends in Pharmacological Sciences. vol. 23, No. 9 pp. 417-425 (2002).

Laredo et al., "Effect of the Protein Kinase C Inhibitor Staurosporine on Chemosensitivity to Daunorubicin of Normal and Leukemic Fresh Myeloid Cells," Blood. vol. 84, No. 1 pp. 229-237 (1994).

Luo et al., "Blocking CHK1 Expression Induces Apoptosis and Abrogates the G2 Checkpoint Mechanism," Neoplasia. vol. 3, No. 5 pp. 411-419 (2001).

McInnes et al., "Progress in the Evaluation of CDK Inhibitors as Anti-Tumor Agents," Drug Discovery Today. vol. 13 pp. 875-881 (2008).

Menu et al., "A Novel Therapeutic Combination Using PD 0332991 and Bortezomib: Study in the 5T33MM Myeloma Model," Cancer Research. vol. 68, No. 14 pp. 5519-5523 (2008).

Michaud et al., "Pharmacologic Inhibition of Cyclin-Dependent Kinases 4 and 6 Arrests the Growth of Glioblastoma Multiforme Intracranial Xenografts," Cancer Research. vol. 70, No. 8 pp. 3228-3238 (2010).

Notification of Transmittal of the International Preliminary Examination Report (PCT Rule 71.1) corresponding to PCT/US2010/034816 dated May 25, 2012.

Notification of Transmittal of the International Preliminary Examination Report on Patentabilty (Chapter II of the Patent Cooperation Treaty) corresponding to International Patent Application No. PCT/US2009/059254 dated Dec. 6, 2011.

Notification of Transmittal of the International Preliminary Examination Report on Patentability (Chapter II of the Patent Cooperation Treaty) corresponding to International Patent Application No. PCT/US2009/059281 dated Nov. 23, 2011.

Notification of Transmittal of the International Search Report and the Written Opinion of the International Searching Authority, or the Declaration corresponding to International Patent Application No. PCT/US2009/059254 dated May 6, 2010.

Notification of Transmittal of the International Search Report and the Written Opinion of the International Searching Authority, or the Declaration corresponding to International Patent Application No. PCT/US2009/059281 dated Dec. 24, 2010.

Notification of Transmittal of the International Search Report and the Written Opinion of the International Searching Authority, or the

(56) References Cited

OTHER PUBLICATIONS

Declaration corresponding to International Patent Application No. PCT/US2010/034816 dated Jan. 28, 2011.
O'Dwyer et al., "A phase I dose escalation trial of a daily oral CDK 4/6 inhibitor PD-0332991," J. Clin. Oncol. vol. 25, No. 18 (ASCO, Chicago, Illinois, 2007) [Abstract].
Official Action corresponding to Chinese Patent Application No. 200980148408.0 dated Oct. 31, 2012.
Official Action corresponding to Chinese Patent Application No. 200980148409.5 dated Oct. 31, 2012.
Official Action corresponding to Chinese Patent Application No. 201080031866.9 dated Mar. 5, 2013.
Official Action corresponding to Israeli Patent Application No. 212103 dated Nov. 13, 2012.
Official Action corresponding to Israeli Patent Application No. 212104 dated Nov. 13, 2012.
Official Action corresponding to Israeli Patent Application No. 216315 dated Jan. 16, 2013.
Official Action corresponding to Japanese Patent Application No. 2011-530243 dated Feb. 22, 2013.
Official Action corresponding to U.S. Appl. No. 13/122,017 dated Nov. 20, 2012.
Official Action corresponding to U.S. Appl. No. 13/122,017 dated Jan. 17, 2013.
Official Action corresponding to U.S. Appl. No. 13/122,017 dated Oct. 10, 2013.
Official Action corresponding to U.S. Appl. No. 13/122,061 dated Oct. 25, 2012.
Official Action corresponding to U.S. Appl. No. 13/122,061 dated Feb. 12, 2013.
Official Action corresponding to U.S. Appl. No. 13/122,061 dated Aug. 23, 2013.
Official Action corresponding to U.S. Appl. No. 13/319,828 dated Dec. 12, 2012.
Official Action corresponding to U.S. Appl. No. 13/319,828 dated Jun. 11, 2013.
Ojeda et al., "Role of protein kinase-C in thymocyte apoptosis induced by irradiation," Int. J. Radiat. Biol. vol. 61, No. 5 pp. 663-667 (1992).
Pawlik et al., "Role of Cell Cycle in Mediating Sensitivity to Radiotherapy," Int. J. Radiation Oncology Biol. Phys. vol. 59, pp. 928-942 (2004).
Ramsey et al., "Expression of p16$^{Ink4a}$ Compensates for p18$^{Ink4c}$ Loss in Cyclin-Dependent Kinase 4/6-Dependent Tumors and Tissues," Cancer Research. vol. 67, No. 10 pp. 4732-4741 (2007).
Seed, T. M., "Radiation Protectants: Current Status and Future Prospects," Health Physics. vol. 89 pp. 531-545 (2005).
Sharpless et al., "Both products of the mouse Ink4a/Arf locus suppress melanoma formation in vivo," Oncogene. vol. 22 pp. 5055-5059 (2003).
Sicinski, P., "Cyclins and Cyclin-Dependent Kinases as Targets for Protection Against Radiation," Abstract downloaded from http://projectreporter.nih.gov/project_info_description.cfm on Sep. 28, 2009.
Sinclair, W.K., and Morton, R.A., "X-Ray Sensitivity during the Cell Generation Cycle of Cultured Chinese Hamster Cells," Radiation Research. vol. 29 pp. 450-474 (1966).
Soni et al., "Selective In Vivo and In Vitro Effects of a Small Molecule Inhibitor of Cyclin-Dependent Kinase 4," Journal of the National Cancer Institute. vol. 93, No. 6 pp. 436-446 (2001).
STN Registry No. 571190-30-2. "PD 0332991". Retreived from STN Feb. 7, 2013. 1 page.
Teyssier et al., "Cell cycle regulation after exposure to ionizing radiation," Bulletin du Cancer. vol. 86, No. 4 pp. 345-357 (1999) [Abstract].
Tsou et al., "4-(Phenylaminomethylene)isoquinoline-1,3(2H,4H)-diones as Potent and Selective Inhibitors of the Cyclin-Dependent Kinase 4 (CDK4)," Journal of Medicinal Chemistry,: vol. 51, No. 12 pp. 3507-3525 (2008).
Tsou et al., "Discovery of 4-(Benzylaminomethylene)isoquinoline-1,3-(2H,4H)-diones and 4-[(Pyridylmethyhaminomethylene]isoquinoline-1,3(2H,4H)-diones as Potent and Selective Inhibitors of the Cyclin-Dependent Kinase 4," Journal of Medicinal Chemistry. vol. 52, No. 8 pp. 2289-2310 (2009).
Uckun et al., "In Vivo Radioprotective Effects of Recombinant Human Granulocyte Colony-Stimulating Factor in Lethally Irradiated Mice," Blood. vol. 75, No. 3 pp. 638-645 (1990).
Wang et al., "Protein kinase inhibitor staurosporine enhances cytotoxicity of antitumor drugs to cancer cells," Yao Xue Xue Bao. vol. 31, No. 6 pp. 411-415 (1996) [Abstract].
Weiss, J.F., and Landauer, M.R., "History and development of radiation-protective agents," Int. J. Radiat. Biol. vol. 85, No. 7 pp. 539-573 (2009).
Zhang et al., "Sensitization of C6 glioma cells to radiation by staurosporine, a potent protein kinase C inhibitor," Journal of Neuro-Oncology. vol. 15 pp. 1-7 (1993).
Advisory Action corresponding to U.S. Appl. No. 13/122,017 dated Jul. 23, 2015.
Advisory Action corresponding to U.S. Appl. No. 13/122,017 dated Jun. 24, 2015.
Advisory Action corresponding to U.S. Appl. No. 14/103,359 dated Apr. 29, 2016.
Communication pursuant to Article 94(3) EPC corresponding to European Patent Application No. 10 775 575.3-1456 dated Oct. 13, 2014.
Communication under Rule 71(3) EPC corresponding to European Patent Application No. 10 775 575.3-1456 dated Jun. 26, 2015.
Daemen et al., "Apoptosis and Inflammation in Renal Reperfusion Injury," Transplantation, vol. 73, No. 11, pp. 1693-1700 (2002).
Decision to grant a European patent pursuant to Article 97(1) EPC corresponding to Application No. 10775575.3-1456 dated Dec. 10, 2015.
Dickson, "Molecular Pathways: CDK4 Inhibitors for Cancer Therapy," American Association for Cancer Research. vol. 20, pp. 3379-3383 (2014).
Dirocco et al., "CDK4/6 Inhibition Induces Epithelial Cell Cycle Arrest and Ameliorates Acute Kidney Injury," American Journal of Physiology: Renal Physiology, vol. 306, No. 4, pp. F379-F388 (2014).
Engler et al., "The Development of Potent and Selective Bisarylmaleimide GSK3 inhibitors," Biorg. Med. Chem. Lett. vol. 15, No. 4, pp. 899-903 (2005).
Extended European Search Report corresponding to European Patent Application No. 11842009.0-1453 dated Jan. 27, 2015.
Extended European Search Report corresponding to European Patent Application No. 15196712.2-1456 dated Feb. 29, 2016.
Hara et al., "Regulation of p16CDKN2 Expression and Its Implications for Cell Immortalization and Senescence," Molecular and Cellular Biology. vol. 16, No. 3 pp. 859-867 (1996).
Invitation pursuant to Rule 63(1) EPC corresponding to European Patent Application No. 11 842 009.0-1453 dated Sep. 19, 2014.
Johnson, N., and Shapiro, G.I., "Cyclin-dependent kinase 4/6 inhibition in cancer therapy," Cell Cycle. vol. 11, No. 21 p. 3913 (2012).
Mahboobi et al. "Synthesis of Pyrrolidin-2-Ones and of Staurosporine Aglycon (K-252c) by Intermolecular Michael Reaction". J. Org. Chem. vol. 64 pp. 4697-4704 (1999).
Notice of Publication corresponding to European Application No. 15196712.2-1466 dated May 4, 2016.
Official Action correponding to European Patent Application No. 10 775 575.3-1456 dated Mar. 31, 2014.
Official Action corresponding to Chinese Patent Application No. 200980148408.0 dated Sep. 16, 2013.
Official Action corresponding to Chinese Patent Application No. 200980148409.5 dated Sep. 16, 2013.
Official Action corresponding to Chinese Patent Application No. 201080031866.9 dated Nov. 21, 2013.
Official Action corresponding to Chinese Patent Application No. 201180065126.1 dated Jul. 3, 2014.
Official Action corresponding to European Patent Application No. 09 818 530.9-1453 dated Jul. 7, 2015.

(56) References Cited

OTHER PUBLICATIONS

Official Action corresponding to European Patent Application No. 09 823 989.0-1464 dated Feb. 12, 2015.
Official Action corresponding to European Patent Application No. 09 823 989.0-1464 dated May 8, 2014.
Official Action corresponding to Japanese Patent Application No. 2011-530243 dated Jan. 20, 2014.
Official Action corresponding to Japanese Patent Application No. 2011-530251 dated Dec. 26, 2013.
Official Action corresponding to U.S. Appl. No. 13/122,017 dated Apr. 8, 2016.
Official Action corresponding to U.S. Appl. No. 13/122,017 dated Mar. 16, 2015.
Official Action corresponding to U.S. Appl. No. 13/122,017 dated May 12, 2014.
Official Action corresponding to U.S. Appl. No. 14/103,359 dated Dec. 21, 2015.
Official Action corresponding to U.S. Appl. No. 14/103,359 dated Jan. 28, 2015.
Official Action corresponding to U.S. Appl. No. 14/495,381 dated Feb. 4, 2015.
Official Action corresponding to U.S. Appl. No. 14/495,381 dated May 19, 2015.
Official Action corresponding to U.S. Appl. No. 14/495,381 dated Nov. 18, 2015.
Official Action correspondiong to U.S. Appl. No. 14/103,359 dated Jul. 9, 2015.
Pabla et al., "Mitigation of acute kidney injury by cell-cycle inhibitors that suppress both CDK4/6 and OCT2 functions," PNAS. vol. 112, No. 16, pp. 5231-5236 (2015).
Price, "Dependence of Cisplatin-Induced Cell Death In Vitro and In Vivo on Cyclin-Dependent Kinase 2," Journal of the American Society of Nephrology, vol. 17, No. 9, pp. 2434-2442 (2006).
Retzer-Lidl et al. "Inhibition of CDK4 Impairs Proliferation of Pancreatic Cancer Cells and Sensitizes Towards TRAIL-Induced Apoptosis via Downregulation of Survivin". Int. J. Cancer vol. 121 pp. 66-75 (2007).
Schmidt et al., "Protection against chemotherapy-induced cytotoxicity by cyclin-dependent kinase inhibitors (CKI) in CKI-responsive cells compared with CKI-unresponsive cells," Oncogene. vol. 20 pp. 6164-6171 (2001).
Search Report corresponding to Chinese Patent Application No. 200980148408.0 dated Sep. 16, 2013.
Search Report corresponding to Chinese Patent Application No. 200980148409.5 dated Sep. 16, 2013.
Stone et al., "Reversible, p16-mediated Cell Cycle Arrest as Protection from Chemotherapy," Cancer Research. vol. 56 pp. 3199-3202 (1996).
Chen et al., "Protection of Normal Proliferating Cells Against Chemotherapy by Staurosporine-Mediated, Selective, and Reversible $G_1$ Arrest," Journal of the National Cancer Institute. vol. 92, No. 24 pp. 1999-2008 (2000).
Davis et al., "Prevention of Chemotherapy-Induced Alopecia in Rats by CDK Inhibitors," Science. vol. 291 pp. 134-137 (2001).
Engler et al., "Novel, Potent and Selective Cyclin D1/CDK4 Inhibitors: Indolo[6,7-a]pyrrolo[3,4-c]carbazoles," Bioorganic & Medicinal Chemistry Letters. vol. 13 pp. 2261-2267 (2003).
Honma et al., "A Novel Approach for the Development of Selective Cdk4 Inhibitors: Library Design Based on Locations of Cdk4 Specific Amino Acid Residues," J. Med. Chem. vol. 44, No. 26 pp. 4628-4640 (2001).
Honma et al., "Structure-Based Generation of a New Class of Potent Cdk4 Inhibitors: New de Novo Design Strategy and Library Design," J. Med. Chem. vol. 44, No. 26 pp. 4615-4627 (2001).
Ikuta et al., "Crystallographic Approach to Identification of Cyclin-dependent Kinase 4 (CDK4)-specific Inhibitors by Using CDK4 Mimic CDK2 Protein," The Journal of Biological Chemistry, vol. 276, No. 29 pp. 27548-27554 (2001).
Kubo et al., "The p16 Status of Tumor Cell Lines Identifies Small Molecule Inhibitors Specific for Cyclin-dependent Kinase 4," Clinical Cancer Research. vol. 5, No. 12 pp. 4279-4286 (1999).
Notification Concerning Transmittal of International Preliminary Report on Patentability (Chapter I of the Patent Cooperation Treaty) corresponding to International Patent Application No. PCT/US2011/061202 dated May 30, 2013.
Notification of Transmittal of the International Search Report and the Written Opinion of the International Searching Authority, or the Declaration corresponding to International Patent Application No. PCT/US2011/061202 dated May 16, 2012.
Sanchez-Martinez et al., "Aryl[a]pyrrolo[3,4-c]carbazoles as Selective Cyclin D1-CDK4 Inhibitors," Bioorganic & Medicinal Chemistry Letters. vol. 13 pp. 3835-3839 (2003).
Sanchez-Martinez et al., "Studies on Cyclin-Dependent Kinase Inhibitors: Indolo-[2,3-a]pyrrolo[3,4-c]carbazoles versus Bis-indolylmaleimides," Bioorganic & Medicinal Chemistry Letters. vol. 13 pp. 3841-3846 (2003).
Shimamura et al., "Identification of potent 5-pyrimidinyl-2-aminothiazole CDK4, 6 inhibitors with significant selectivity over CDK1, 2, 5, 7, and 9," Bioorganic & Medicinal Chemistry Letters. vol. 16 pp. 3751-3754 (2006).
Toogood et al., "Discovery of a Potent and Selective Inhibitor of Cyclin-Dependent Kinase 4/6," Journal of Medicinal Chemistry. vol. 48, No. 7 pp. 2388-2406 (2005).
Tu et al., "New potential inhibitors of cyclin-dependent kinase 4: Design and synthesis of pyrido[2,3-d]pyrimidine derivatives under microwave irradiation," Bioorganic & Medicinal Chemistry Letters. vol. 16 pp. 3578-3581 (2006).
VanderWel et al., "Pyrido[2,3-d]pyrimidin-7-ones as Specific Inhibitors of Cyclin-Dependent Kinase 4," Journal of Medicinal Chemistry. vol. 48, No. 7 pp. 2371-2387 (2005).
Zhu et al., "Synthesis of Quinolinyl/Isoquinolinyl[a]pyrrolo [3,4-c] Carbazoles as Cyclin D1/CDK4 Inhibitors," Bioorganic & Medicinal Chemistry Letters. vol. 13 pp. 1231-1235 (2003).
Zhu et al., "Synthesis, Structure-Activity Relationship, and Biological Studies of Indolocarbazoles as Potent Cyclin D1-CDK4 Inhibitors," Journal of Medicinal Chemistry. vol. 46, No. 11 pp. 2027-2030 (2003).
Notice of Allowance Corresponding to U.S. Appl. No. 14/103,359 dated Jan. 13, 2017.
Official Action corresponding to U.S. Appl. No. 14/103,359 dated Jul. 28, 2016.
Official Action corresponding to U.S. Appl. No. 13/122,017 dated Jan. 20, 2017.
Walkley et al., "Negative cell-cycle regulators cooperatively control self-renewal and differentiation of haematopoietic stem cells." Nature Cell Biology,7:172-178 (2005).
Communication pursuant to Article 94(3) EPC corresponding to European Application No. 15 196 712.2 dated Jan. 17, 2017.
Deep et al., "New combination therapies with cell-cycle agents," Current Opinion in Investigational Drugs, vol. 9, No. 6, pp. 591-604 (2008).
Official Action corresponding to U.S. Appl. No. 14/495,381 dated Mar. 24, 2017.

\* cited by examiner

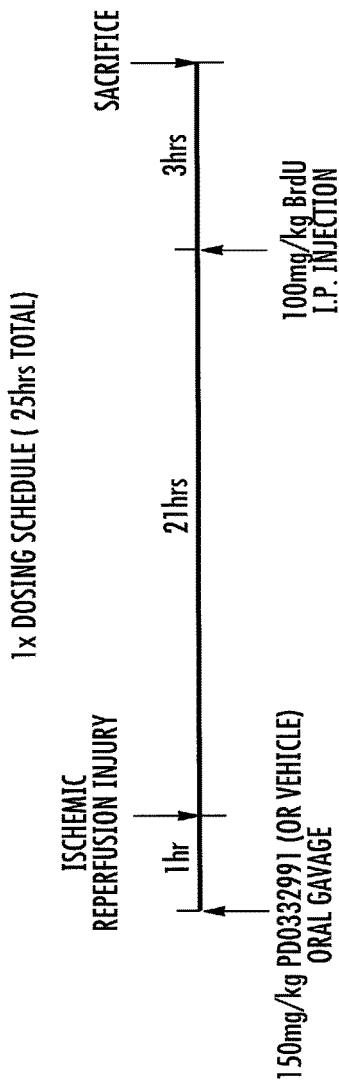
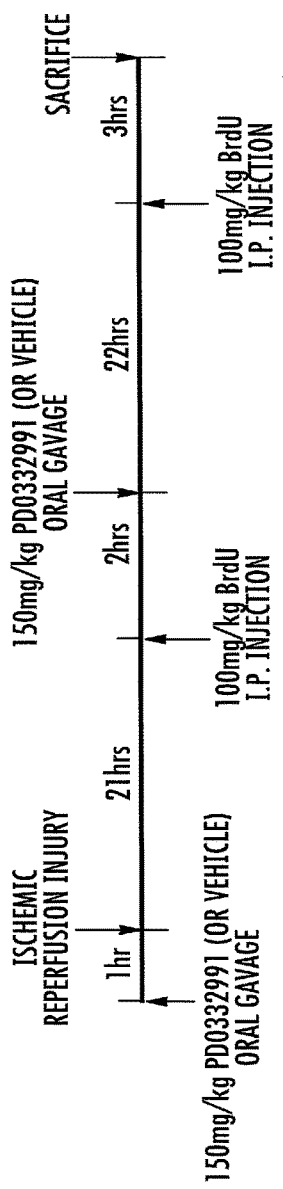
FIG. 3A
FIG. 3B

PROTECTION OF RENAL TISSUES FROM ISCHEMIA THROUGH INHIBITION OF THE PROLIFERATIVE KINASES CDK4 AND CDK6

PRIORITY CLAIM

This application claims the benefit of U.S. Provisional Patent Application Ser. No. 61/458,140 filed Nov. 17, 2010, the disclosure of which is incorporated herein by reference in its entirety.

GOVERNMENT INTEREST

The presently disclosed subject matter was made with U.S. Government support under Grant No. R43 AI084284 awarded by the National Institutes of Health. Thus, the U.S. Government has certain rights in the presently disclosed subject matter.

TECHNICAL FIELD

The presently disclosed subject matter relates to methods and compositions for protecting healthy cells from damage from ischemia. For example, the presently disclosed subject matter relates to uses of cyclin dependent kinase 4/6 (CDK4/6) inhibitors to induce pharmacologic quiescence in certain tissues and/or cells, such as kidney, within a mammalian subject and thereby enhancing clinical outcomes for that subject.

ABBREVIATIONS

%=percentage
μg=microgram
μL=microliters
μM=micromolar
BrdU=5-bromo-2-deoxyuridine
CAT=computerized axial tomography
CDK=cyclin-dependent kinase
CDK4/6=cyclin dependent kinase 4 and/or cyclin-dependent kinase 6
CT=computed tomography
dL=deciliter
DMSO=dimethyl sulfoxide
g=gram
h=hours
$IC_{50}$=50% inhibitory concentration
i.p.=intraperitoneal
IRI=ischemia reperfusion injury
kg=kilogram
mg=milligrams
nM=nanomolar
PD=6-acetyl-8-cyclopentyl-5-methyl-2-(5-piperazin-1-yl-pyridin-2-ylamino)-8H-pyrido-[2,3-d]-pyrimidin-7-one (also referred to as PD 0332991)
RLU=relative light units
SEM=standard error of the mean

BACKGROUND

Because no therapies exist that are proven to protect kidney from ischemic injury, management currently includes supporting the patient until such time as the kidney is able to heal itself. Management strategies include the use of diuretics to regulate volume status, phosphorous binders and, when needed, dialysis. Of note, none of these therapies alter the natural history of the kidney repair process, and some evidence suggests that diuretics and dialysis might even worsen kidney damage. Accordingly, there is an ongoing need for practical methods to protect subjects who are scheduled to incur, are at risk for incurring, or who have already incurred, ischemia and/or events related thereto.

SUMMARY

In some embodiments, the presently disclosed subject matter provides a method of mitigating injury from ischemia and/or a related event in a cell or tissue in a subject in need of treatment thereof prior to or following exposure of the cell or tissue to ischemia and/or a related event, wherein the method comprises administering to the subject a pharmaceutically effective amount of a compound that inhibits cyclin dependent kinase 4 (CDK4) and/or cyclin dependent kinase 6 (CDK6), and wherein the cell or tissue is characterized by proliferation after injury that is CDK4/6 dependent.

In some embodiments, the presently disclosed subject matter provides a method of mitigating injury from ischemia and/or a related event in a renal cell or renal tissue in a subject in need of treatment thereof prior to or following exposure of the cell or tissue to ischemia and/or a related event, wherein the method comprises administering to the subject a pharmaceutically effective amount of a compound that inhibits cyclin dependent kinase 4 (CDK4) and/or cyclin dependent kinase 6 (CDK6).

In some embodiments, the compound that inhibits CDK4 and/or CDK6 is administered to the subject prior to the subject being exposed to the ischemia and/or a related event, at the same time the subject is being exposed to the ischemia and/or a related event, or after exposure of the subject to ischemia and/or a related event. In some embodiments, the compound that inhibits CDK4 and/or CDK6 is administered to the subject between about 24 and about 48 hours after exposure of the subject to ischemia and/or a related event.

In some embodiments, the compound that inhibits CDK4 and/or CDK6 is a selective CDK4 and/or CDK6 inhibitor. In some embodiments, the selective CDK4/6 inhibitor is a poor inhibitor of cyclin dependent kinases other than CDK4 and/or CDK6.

In some embodiments, the ischemia-inducing event is cardiac surgery, or other surgery associated with hypotensive episodes. In some embodiments, the ischemia inducing event is the administration of radio-contrast agents as used for CT scans, pylorograms and artiography. In some embodiments, the ischemia-inducing event is trauma associated with a period of hypovolemia (e.g., due to blood loss) and/or hypotension.

In some embodiments, the ischemia inducing event is administration of a medicine or agent, such as aspirin, ibuprofen, tacrolimus, and/or cyclosporine, that decreases renal blood flow. In some embodiments, the ischemia-inducing event is acute tissue ischemia or infarction as caused by arterial embolus or in situ arterial or venous thrombosis. In some embodiments, the ischemia-inducing event is torsion of a volvulus or other transient anatomic disruption of organ blood flow. In some embodiments, the ischemia-inducing event is harvesting, transport and/or cold-storage of a kidney allograft prior to transplantation.

It is an object of the presently disclosed subject matter to provide methods of protecting healthy cells in subjects from the effects of ischemia by administering to the subject an effective amount of a CDK4/6 inhibitor compound.

An object of the presently disclosed subject matter having been stated hereinabove, and which is achieved in whole or in part by the presently disclosed subject matter, other objects will become evident as the description proceeds when taken in connection with the accompanying drawings as best described hereinbelow.

BRIEF DESCRIPTION OF THE DRAWINGS

FIG. 3A is a schematic diagram showing a dosing schedule for studies of 5-bromo-2-deoxyuridine (BrdU) incorporation into epithelial cells following ischemic reperfusion injury after a single dosing of a CDK4/6 inhibitor. Mice were treated with 6-acetyl-8-cyclopentyl-5-methyl-2-(5-piperazin-1-yl-pyridin-2-ylamino)-8H-pyrido-[2,3-d]pyrimidin-7-one (PD0332991; 150 mg/kg) or vehicle (sodium lactate buffer) by oral gavage one hour before ischemic reperfusion injury. BrdU (100 mg/kg) was administered via i.p. injection 21 hours after injury. Mice were sacrificed 3 hours after the BrdU injection, and BrdU incorporation into the renal epithelial cells was quantified.

FIG. 3B is a schematic diagram showing a dosing schedule for studies of 5-bromo-2-deoxyuridine (BrdU) incorporation into epithelial cells following ischemic reperfusion injury after two doses of a CDK4/6 inhibitor. Mice were treated with 6-acetyl-8-cyclopentyl-5-methyl-2-(5-piperazin-1-yl-pyridin-2-ylamino)-8H-pyrido-[2,3-d]pyrimidin-7-one (PD0332991; 150 mg/kg) or vehicle (sodium lactate buffer) by oral gavage one hour before ischemic reperfusion injury. BrdU (100 mg/kg) was administered via i.p. injection 21 hours after injury. After a further two hours, the mice were treated a second time with either PD0332991 or vehicle. Twenty-two hours following the second dosing, mice received a second injection of BrdU. Three hours following the second injection of BrdU, the mice were sacrificed and BrdU incorporation into the renal epithelial cells was quantified.

DETAILED DESCRIPTION

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

Throughout the specification and claims, a given chemical formula or name shall encompass all active optical and stereoisomers, as well as racemic mixtures where such isomers and mixtures exist.

In some embodiments, the presently disclosed subject matter allows for protection of kidney from the acute toxic effects of ischemia and kidney toxins that induce ischemia. A small molecule kinase inhibitor that is orally available and non-toxic is administered before, during or immediately after renal injury to enhance kidney regeneration at later time points.

Figure 4B:
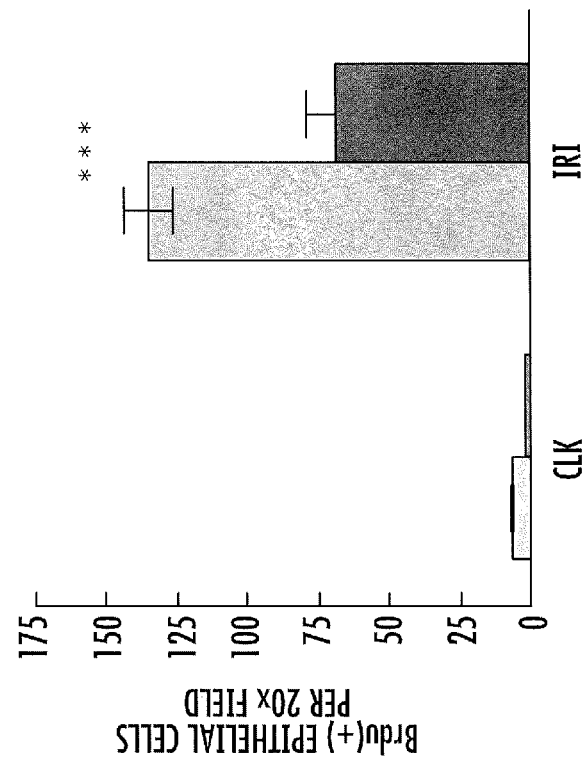
FIG. 4B is a bar graph showing that treatment with a CDK4/6 inhibitor prevents epithelial cells from entering S-phase 48 hours after ischemic injury. The right-hand side of the graph shows averaged data of 5-bromo-2-deoxyuridine (BrdU) positive cells from mice subjected to ischemia reperfusion injury (IRI) and treated with either vehicle (lightly shaded bar, n=5) or with 6-acetyl-8-cyclopentyl-5-methyl-2-(5-piperazin-1-yl-pyridin-2-ylamino)-8H-pyrido-[2,3-d]pyrimidin-7-one (PD0332991; darkly shaded bar, n=6) two times according to the dosing schedule shown in FIG. 3B. Two-way ANOVA, ***$p<0.001$ (Bonferroni's post hoc test). The left-hand side of the graph show data for mice treated with vehicle (lightly shaded bar) or PD0332991 (darkly shaded bar) according to the dosing schedule, only not subjected to ischemia reperfusion injury (CLK).
Figure 4A:
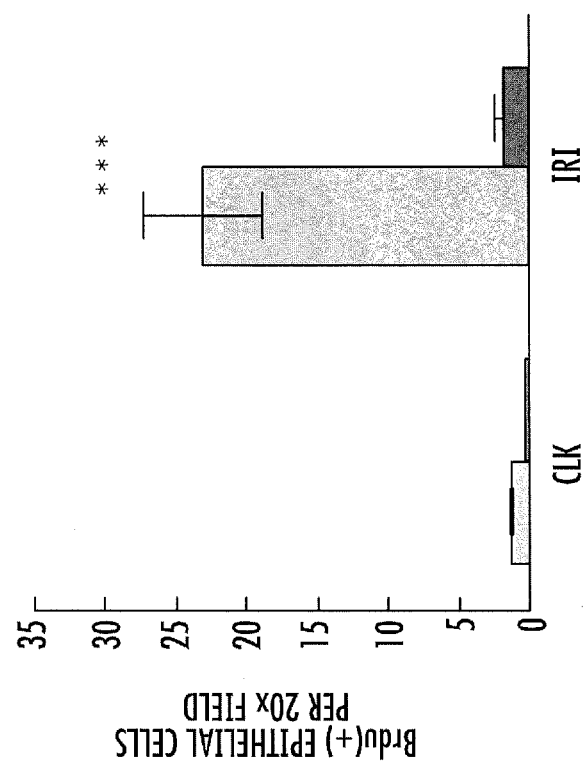
FIG. 4A is a bar graph showing that treatment with a CDK4/6 inhibitor prevents epithelial cells from entering S-phase 24 hours after ischemic injury. The right-hand side of the graph shows averaged data of 5-bromo-2-deoxyuridine (BrdU) positive cells from 5 mice treated with vehicle (lightly shaded bar) and 6 mice treated one time with 6-acetyl-8-cyclopentyl-5-methyl-2-(5-piperazin-1-yl-pyridin-2-ylamino)-8H-pyrido-[2,3-d]pyrimidin-7-one PD0332991; darkly shaded bar) one hour before ischemia reperfusion injury (IRI) according to the dosing schedule shown in FIG. 3A. Two-way ANOVA, ***$p<0.001$ (Bonferroni's post hoc test). The left-hand side of the graph show data for mice treated with vehicle (lightly shaded bar) or PD0332991 (darkly shaded bar) but not subjected to ischemia reperfusion injury (CLK).
Figure 5:
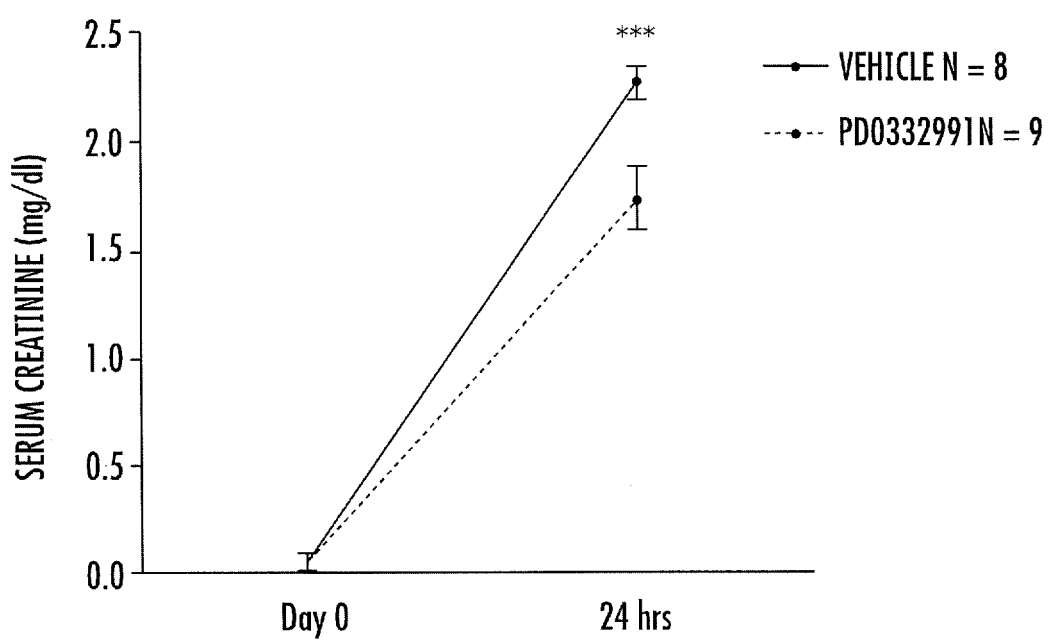
FIG. 5 is a line graph showing that treatment with 6-acetyl-8-cyclopentyl-5-methyl-2-(5-piperazin-1-yl-pyridin-2-ylamino)-8H-pyrido-[2,3-d]pyrimidin-7-one (PD0332991) significantly reduces serum creatinine levels 24 hours after bilateral ischemia reperfusion injury. Baseline serum creatinine levels were taken 7 days prior to surgery and there was no appreciable baseline differences between vehicle treated and drug treated groups (0.050 mg/dL±0.027 and 0.044 mg/dL±0.044, respectively). 24 hours after surgery serum creatinine in the vehicle group was 2.27 mg/dL±0.0732 and 1.74 mg/dL±0.143 in the drug treated group. N=8 in the vehicle group and N=9 in the drug treated group. *** $p<0.001$ analyzed by two-way ANOVA with Bonferroni post-test.

It has been shown that kidney proliferation is induced in response to renal injury. As disclosed herein for the first time, it appears that kidney proliferation following ischemia depends on the kinase activity of CDK4/6. For example, as shown in FIGS. 4A and 4B, kidney cell proliferation following ischemia can be decreased by administration of a CDK4/6 inhibitor. Further, during the period of time around renal injury, certain circulating nephrotoxins can further increase renal injury in a cell cycle dependent manner. Therefore, transiently holding renal epithelial cells in G1 through the pharmacologic use of CDK4/6 inhibitors (pharmacologic quiescence or PQ) can allow for enhanced kidney renal repair after circulating nephrotoxins have been cleared. See FIG. 5. Transient PQ at the time of ischemic insult will enhance subsequent kidney recovery. Thus, the presently disclosed subject matter capitalizes on the finding that proliferating cells are highly sensitive to exogenous toxins, and therefore transient PQ is therapeutic. The presently disclosed subject matter can involve administration (e.g., oral or IV) of a CDK4/6 inhibitor (e.g., a selective CDK4/6 inhibitor) prior to, at the time of, or after (such as within 20 hours) of renal ischemic injury. Therapeutic levels of CDK4/6 inhibitor can be maintained until the conditions inducing the renal injury have been reversed (generally 24-48 hours). CDK4/6 inhibitor can then be withdrawn (using compounds that are not exclusively cleared by the kidney) and renal regenerative proliferation can ensue. For example, PQ can be induced prior to surgery associated with hypotension (e.g. cardiac bypass grafting) or prior to transport of a renal allograft (e.g. cold-ischemia in kidney transplantation) or prior to the use of iodine-containing radiocontrast agents (which induce renal ischemia). PQ can be reversed 24-48 hours after such insults when nephrotoxins have been cleared and/or systemic blood pressure has been restored.

Thus, the presently disclosed subject matter pertains in part to the observation that pharmacological quiescence provides protection against forms of renal insult, particularly renal ischemia. Renal ischemia can result, for example from low blood pressure for any reason (e.g. during surgery or traumatic shock), and is also the mechanism of injury of several nephrotoxic drugs (such as but not limited to iodine-containing contrast agents used in CAT scans).

I. Definitions

While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. Thus, for example, reference to "a compound" or "a cell" includes a plurality of such compounds or cells, and so forth.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

The term "and/or" when used in describing two items or conditions, e.g., CDK4 and/or CDK6, refers to situations where both items or conditions are present or applicable and to situations wherein only one of the items or conditions is present or applicable. Thus, a CDK4 and/or CDK6 inhibitor can be a compound that inhibits both CDK4 and CDK6, a compound that inhibits only CDK4, or a compound that only inhibits CDK6.

By "healthy cell" or "normal cell" is meant any cell in a subject that does not display characteristics, symptoms and/or markers of a disease (such as, but not limited to, cancer or another proliferative disease). In some embodiments, the healthy cell is a renal cell. In some embodiments, the healthy cell is a cell in a tissue, such as kidney. In some embodiments, the cell or tissue is characterized by proliferation after injury that is CDK4/6 dependent, and in some embodiments the injury is ischemia-related.

"Ischemia" can refer to inadequate blood flow to a tissue or organ, which results in the tissue or organ's inability to meet demands for metabolism. Reperfusion (resumption of blood flow) to the ischemic organ or tissue can lead to the production of excessive amounts of reactive oxygen species (ROS) and reactive nitrogen species (RNS), thus causing oxidative stress which results in a series of events such as alterations in mitochondrial oxidative phosphorylation, depletion of ATP (which also occurs during and as a result of ischemia), an increase in intracellular calcium and activation of protein kinases, phosphatases, proteases, lipases and nucleases leading to loss of cellular function/integrity.

Ischemia reperfusion injury (IRI) refers to an injury which occurs after blood circulation is restarted in a tissue subjected to ischemia (e.g., when an organ is excised by operation and re-attached, as in a transplant or auto-transplant). By way of additional example and not limitation, such injury also occurs when blood circulation is restarted after being stopped for the transplantation of an organ; after a coronary artery is treated with percutaneous transluminal coronary angioplasty (PTCA), stent, or bypass after myocardial infarction; and after administration of a thrombolytic to a stroke patient. Another example is when blood flow to the heart is temporarily stopped for cardiac surgery, often by the concomitant administration of cardioplegia solutions. Another example is interruption of blood flow to a limb for surgery in a bloodless field by an orthopedic surgeon when a tourniquet is inflated on the limb. Such an injury can occur in many tissues, such as, but not limited to, kidney, gut, heart, liver, brain, thyroid, skin, intestinal mucosa, auditory system, lung, bladder, ovary, uterus, testicle, adrenal, gallbladder, pancreas, pancreatic islet, stomach, blood vessel, or muscle (e.g., skeletal, smooth, or cardiac muscle) tissue and combinations thereof. In some embodiments, the injury occurs in heart, lung, kidney tissue or combinations thereof. In some embodiments, the cell or tissue suffering the injury is characterized by proliferation after injury that is CDK4/6 dependent.

In some embodiments, the injury occurs in a kidney cell or tissue. Thus, in some embodiments, the IRI to be treated (e.g., reduced or prevented) by the presently disclosed subject matter can include renal ischemia reperfusion injury. In some embodiments, the kidney cell or tissue is characterized by proliferation after injury that is CDK4/6 dependent.

By "at risk of being exposed to ischemia" is meant a subject scheduled for exposure to ischemia in the future or a subject having a chance of being exposed to ischemia inadvertently in the future.

By "pharmaceutically effect amount of a compound" is meant an amount effective to provide a beneficial result in the subject. In some embodiments, the effective amount is the amount required to temporarily (e.g., for a few hours or days) induce a quiescent state in cells in the subject.

In some embodiments, the compound that inhibits CDK4 and/or CDK6 is free of off-target effects, such as, but not limited to, long term toxicity, anti-oxidant effects and/or estrogenic effects. "Free of" can refer to a CDK4/6 inhibitor compound not having an undesired or off-target effect, particularly when used in vivo or assessed via a cell-based assay.

In some embodiments, "free of" can refer to a selective CDK4/6 inhibitor not having off-target effects such as, but not limited to, long term toxicity, anti-oxidant effects, estrogenic effects, tyrosine kinase inhibitory effects, inhibitory effects on CDKs other than CDK4/6; and/or cell cycle arrest in CDK4/6-independent cells.

A selective CDK4/6 inhibitor that is "substantially free" of off-target effects is a CDK4/6 inhibitor that can have some minor off-target effects that do not interfere with the inhibitor's ability to provide protection from cytotoxic compounds in CDK4/6-dependent cells. For example, a CDK4/6 inhibitor that is "substantially free" of off-target effects can have some minor inhibitory effects on other CDKs (e.g., IC$_{50}$s for CDK1 or CDK2 that are >0.5 µM; >1.0 µM, or >5.0 µM), so long as the inhibitor provides selective G1 arrest in CDK4/6-dependent cells.

By "reduced" or "prevented" or grammatical variations thereof means, respectively, lessening the effects or keeping the effects from occurring completely. "Mitigating" can refer to reducing and/or preventing.

By "pharmacologic quiescence" is meant a temporary arrest of cell cycling.

In some embodiments, the subject treated in the presently disclosed subject matter is desirably a human subject, although it is to be understood the methods described herein are effective with respect to all vertebrate species (e.g., mammals, birds, etc.), which are intended to be included in the term "subject."

More particularly, provided herein is the treatment of mammals, such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Thus, embodiments of the methods described herein include the treatment of livestock, including, but not limited to, domesticated swine (pigs and hogs), ruminants, horses, and the like.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl)hydrocarbon chains, including for example, methyl, ethyl, propyl, isopropyl, butyl, isobutyl, tert-butyl, pentyl, hexyl, octyl, ethenyl, propenyl, butenyl, pentenyl, hexynyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic moiety that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, carbonyl, acyl, halo, nitro, alkoxycarbonyl, aryloxycarbonyl, aralkoxycarbonyl, acyloxyl, acylamino, arylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

The term "heteroaryl" refers to aryl groups wherein at least one atom of the backbone of the aromatic ring or rings is an atom other than carbon. Thus, heteroaryl groups have one or more non-carbon atoms selected from the group including, but not limited to, nitrogen, oxygen, and sulfur.

As used herein, the term "acyl" refers to an organic carboxylic acid group wherein the —OH of the carboxyl group has been replaced with another substituent (i.e., as represented by RCO—, wherein R is an alkyl or an aryl group as defined herein). As such, the term "acyl" specifically includes arylacyl groups, such as an acetylfuran and a phenacyl group. Specific examples of acyl groups include acetyl and benzoyl.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

The terms "heterocycle" or "heterocyclic" refer to cycloalkyl groups (i.e., non-aromatic, cyclic groups as described hereinabove) wherein one or more of the backbone carbon atoms of a cyclic ring is replaced by a heteroatom (e.g., nitrogen, sulfur, or oxygen). Examples of heterocycles include, but are not limited to, tetrahydrofuran, tetrahydropyran, morpholine, dioxane, piperidine, piperazine, and pyrrolidine.

"Alkoxyl" or "alkoxy" refers to an alkyl-O— group wherein alkyl is as previously described. The term "alkoxyl" as used herein can refer to, for example, methoxyl, ethoxyl, propoxyl, isopropoxyl, butoxyl, t-butoxyl, and pentoxyl. The term "oxyalkyl" can be used interchangably with "alkoxyl".

"Aryloxyl" or "aryloxy" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl- group wherein aryl and alkyl are as previously described, and included substituted aryl and substituted alkyl. Exemplary aralkyl groups include benzyl, phenylethyl, and naphthylmethyl.

"Aralkyloxyl" or "aralkyloxy" refers to an aralkyl-O— group wherein the aralkyl group is as previously described. An exemplary aralkyloxyl group is benzyloxyl.

The term "amino" refers to the —NR'R" group, wherein R' and R" are each independently selected from the group including H and substituted and unsubstituted alkyl, cycloalkyl, heterocycle, aralkyl, aryl, and heteroaryl. In some embodiments, the amino group is —NH$_2$. "Aminoalkyl" and "aminoaryl" refer to the —NR'R" group, wherein R' is as defined hereinabove for amino and R" is substituted or unsubstituted alkyl or aryl, respectively.

"Acylamino" refers to an acyl-NH— group wherein acyl is as previously described.

The term "carbonyl" refers to the —(C=O)— or a double bonded oxygen substituent attached to a carbon atom of a previously named parent group.

The term "carboxyl" refers to the —COOH group.

The terms "halo", "halide", or "halogen" as used herein refer to fluoro, chloro, bromo, and iodo groups.

The terms "hydroxyl" and "hydroxy" refer to the —OH group.

The term "oxo" refers to a compound described previously herein wherein a carbon atom is replaced by an oxygen atom.

The term "cyano" refers to the —CN group.

The term "nitro" refers to the —NO$_2$ group.

The term "thio" refers to a compound described previously herein wherein a carbon or oxygen atom is replaced by a sulfur atom.

II. Compounds and Methods

In some embodiments, the presently disclosed subject matter allows for the protection of the kidney from the acute toxic effects of ischemia and kidney toxins that induce ischemia. A small molecule kinase inhibitor that is orally available and non-toxic is administered before, during or immediately after renal injury to enhance kidney regeneration at later time points. Kidney proliferation is induced in response to renal injury. See FIGS. 4A and 4B. During the period of time around renal injury, certain circulating nephrotoxins will further increase renal injury in a cell cycle dependent manner. Therefore, transiently holding renal epithelial cells in G1 through the pharmacologic use of CDK4/6 inhibitors (pharmacologic quiescence or PQ) will allow for enhanced renal repair after circulating nephrotoxins have been cleared. See FIG. 5. Transient PQ at the time of ischemic insult will enhance subsequent kidney recovery. The discovery capitalizes on the finding that proliferating cells are highly sensitive to exogenous toxins, and therefore transient PQ is therapeutic. The method can involve administration (oral or IV) of a CDK4/6 inhibitor prior to, at the time of, or after (such as within 20 hours) of renal ischemic injury. The CDK4/6 inhibitor can be a selective CDK4/6 inhibitor. Therapeutic levels of CDK4/6 inhibitor can be maintained until the conditions inducing the renal injury have been reversed (generally 24-48 hours). CDK4/6 inhibitor can then be withdrawn (using compounds that are not exclusively cleared by the kidney) and renal regenerative proliferation would ensue. For example, PQ can be induced prior to surgery associated with hypotension (e.g. cardiac bypass grafting) or prior to the use of iodine containing radiocontrast agents. PQ can be reversed 24-48 hours after such insults when nephrotoxins have been cleared and/or systemic blood pressure has been restored.

The kidney is usually a quiescent organ, but is capable of immense repair through cellular proliferation when damaged. The kidney is particularly susceptible to ischemia as a result of decreased blood flow and toxins which reduce renal blood flow. Ischemic injury is followed by a marked increase in renal epithelial proliferation. As shown herein, proliferation following ischemic injury can be inhibited by CDK4/6 inhibitors which induce PQ. See FIGS. 4A and 4B. PQ lasting from 12-72 hours post-injury will allow for the clearance of circulating nephrotoxins produced at the time of renal injury, and thereby facilitate renal recovery.

U.S. Pat. No. 6,369,086 to Davis et al. (hereinafter "the '086 patent") appears to describe that selective CDK inhibitors can be useful in limiting the toxicity of cytotoxic agents and can be used to protect from chemotherapy-induced alopecia. In particular, the '086 patent describes oxindole compounds as specific CDK2 inhibitors. A related journal reference (see Davis et al., *Science*, 291, 134-137 (2001)) appears to describe that the inhibition of CDK2 produces cell cycle arrest, reducing the sensitivity of the epithelium to cell cycle-active antitumor agents and can prevent chemotherapy-induced alopecia. However, this journal reference was later retracted due to the irreproducibility of the results. In contrast to these purported protective effects of selective CDK2 inhibitors, for which a question is raised by the retraction of the journal article, the presently disclosed subject matter relates in some embodiments to protection of tissue and/or cells, such as renal tissue and/or cells, from effects of ischemia.

The protective effects of the CDK4/6 inhibitors can be provided to the subject via pretreatment with the inhibitor (i.e., prior CDK4/6 inhibitor treatment of a subject scheduled to be or at risk of exposure to ischemia).

In some embodiments, the ischemia-inducing event is cardiac surgery, or other surgery associated with hypotensive episodes. In some embodiments, the ischemia inducing event is the administration of radio-contrast agents as used for CT scans, pylorograms and artiography. In some embodiments, the ischemia-inducing episode is renal allograft harvesting (e.g., cadaveric renal allograft harvesting) with cold-ischemia induced during transportation and/or storage of the kidney in the absence of blood flow. In some embodiments the ischemia-inducing event is trauma associated with a period of hypovolemia (e.g., due to bleeding, dehydration, etc.) and/or hypotension. In some embodiments the ischemia-inducing event is administration of a medicine or agent, such as, but not limited to aspirin, ibuprofen, tacrolimus, and/or cyclosporine, that decreases blood flow (e.g., renal blood flow). In some embodiments, the ischemia-inducing event is acute tissue ischemia or infarction as caused by arterial embolus or in situ arterial or venous thrombosis. In some embodiments, the ischemia-inducing event is torsion of a volvulus or other transient anatomic disruption of organ blood flow.

As used herein the term "selective CDK4/6 inhibitor compound" refers to a compound that selectively inhibits at least one of CDK4 and CDK6 or whose predominant mode of action is through inhibition of CDK4 and/or CDK6. Thus, selective CDK4/6 inhibitors are compounds that generally have a lower 50% inhibitory concentration ($IC_{50}$) for CDK4 and/or CDK6 than for other kinases or for other enzymes. In some embodiments, the selective CDK4/6 inhibitor can have an $IC_{50}$ for CDK4 or CDK6 that is at least 2, 3, 4, 5, 6, 7, 8, 9, or 10 times lower than the compound's $IC_{50}$s for other CDKs (e.g., CDK1 and CDK2). In some embodiments, the selective CDK4/6 inhibitor can have an $IC_{50}$ for CDK4 or CDK6 that is at least 20, 30, 40, 50, 60, 70, 80, 90, or 100 times lower than the compound's $IC_{50}$s for other CDKs. In some embodiments, the selective CDK4/6 inhibitor can have an $IC_{50}$ that is more than 100 times or more than 1000 times less than the compound's $IC_{50}$s for other CDKs. In some embodiments, the selective CDK4/6 inhibitor compound is a compound that selectively inhibits both CDK4 and CDK6. In some embodiments, the CDK4/6 inhibitor is not a naturally occurring compound (e.g., an isoflavone). In some embodiments, the CDK4/6 inhibitor is a poor inhibitor (e.g., >1 µM in vitro $IC_{50}$) of one or more tyrosine kinases. In some embodiments, the CDK4/6 inhibitor is a high potency inhibitor of serine and/or theonine kinases. In some embodiments, the CDK4/6 inhibitor is a poor CDK1 inhibitor (e.g., (e.g., >1 µM in vitro $IC_{50}$). In some embodiments, the CDK4/6 inhibitor is characterized by having a 10-fold or 50-fold or 100-fold or greater relative potency for inhibiting CDK4 or CDK6 as compared to CDK1.

In some embodiments, the selective CDK4/6 inhibitor compound is a compound that selectively induces G1 cell cycle arrest in CDK4/6 dependent cells. Thus, when treated with the selective CDK4/6 inhibitor compound according to the presently disclosed methods, the percentage of CDK4/6-dependent cells in the G1 phase increase, while the percentage of CDK4/6-dependent cells in the G2/M phase and S phase decrease. In some embodiments, the selective CDK4/6 inhibitor is a compound that induces substantially pure (i.e., "clean") G1 cell cycle arrest in the CDK4/6-dependent cells (e.g., wherein treatment with the selective CDK4/6 inhibitor induces cell cycle arrest such that the majority of cells are arrested in G1 as defined by standard methods (e.g., propidium iodide staining or others) and with the population of cells in the G2/M and S phases combined being 20%, 15%, 12%, 10%, 8%, 6%, 5%, 4%, 3%, 2%, 1% or less of the total cell population).

While staurosporine, a non-specific kinase inhibitor, has been reported to indirectly induce G1 arrest in some cell types (see Chen et al., *J. Nat. Cancer Inst.*, 92, 1999-2008 (2000)), selective CDK4/6 inhibitors can directly and selectively induce G1 cell cycle arrest in cells, such as renal epithelial cells, to provide protection with reduced long term toxicity and without the need for prolonged (e.g., 48 hour or longer) treatment with the inhibitor prior to exposure to ischemia. In particular, while some nonselective kinase inhibitors can cause G1 arrest in some cell types by decreasing CDK4 protein levels, benefits of the presently disclosed methods are, without being bound to any one theory, believed to be due at least in part to the ability of selective CDK4/6 inhibitors to directly inhibit the kinase activity of CDK4/6 in cells (e.g., renal cells) without decreasing their cellular concentration.

In some embodiments, the selective CDK4/6 inhibitor compound is a compound that is substantially free of off target effects, particularly related to inhibition of kinases other than CDK4 and or CDK6. In some embodiments, the selective CDK4/6 inhibitor compound is a poor inhibitor (e.g., >1 µM $IC_{50}$) of CDKs other than CDK4/6 (e.g., CDK 1 and CDK2). In some embodiments, the selective CDK4/6 inhibitor compound does not induce cell cycle arrest in CDK4/6-independent cells. In some embodiments, the selective CDK4/6 inhibitor compound is a poor inhibitor (e.g., >1 µM $IC_{50}$) of tyrosine kinases. Additional, undesirable off-target effects include, but are not limited to, long term toxicity, anti-oxidant effects, and estrogenic effects.

Anti-oxidant effects can be determined by standard assays known in the art. For example, a compound with no significant anti-oxidant effects is a compound that does not significantly scavenge free-radicals, such as oxygen radicals. The anti-oxidant effects of a compound can be compared to a compound with known anti-oxidant activity, such as genistein. Thus, a compound with no significant anti-oxidant activity can be one that has less than about 2, 3, 5, 10, 30, or 100 fold anti-oxidant activity relative to genistein. Estrogenic activities can also be determined via known assays. For instance, a non estrogenic compound is one that does not significantly bind and activate the estrogen receptor. A compound that is substantially free of estrogenic effects can be one that has less than about 2, 3, 5, 10, 20, or 100 fold estrogenic activity relative to a compound with estrogenic activity, e.g., genistein.

CDK4/6 inhibitors that can be used according to the presently disclosed methods include any known small molecule (e.g., <1000 Daltons, <750 Daltons, or less than <500 Daltons) CDK4/6 inhibitor, or pharmaceutically acceptable salt thereof. In some embodiments, the inhibitor is a non-naturally occurring compound (i.e., a compound not found in nature). Several classes of chemical compounds have been reported as having CDK4/6 inhibitory ability (e.g., in cell free assays). Selective CDK4/6 inhibitors useful in the presently disclosed methods can include, but are not limited to, pyrido[2,3-d]pyrimidines (e.g., pyrido[2,3-d]pyrimidin-7-ones and 2-amino-6-cyano-pyrido[2,3-d]pyrimidin-4-ones), triaminopyrimidines, aryl[a]pyrrolo[3,4-d]carbazoles, nitrogen-containing heteroaryl-substituted ureas, 5-pyrimidinyl-2-aminothiazoles, benzothiadiazines, acridinethiones, and isoquinolones.

In some embodiments, the pyrido[2,3-d]pyrimidine is a pyrido[2,3-d]pyrimidinone. In some embodiments the pyrido[2,3-d]pyrimidinone is pyrido[2,3-d]pyrimidin-7-one. In some embodiments, the pyrido[2,3-d]pyrimidin-7-one is substituted by an aminoaryl or aminoheteroaryl group. In some embodiments, the pyrido[2,3-d]pyrimidin-7-one is substituted by an aminopyridine group. In some embodiments, the pyrido[2,3-d]pyrimidin-7-one is a 2-(2-pyridinyl) amino pyrido[2,3-d]pyrimidin-7-one. For example, the pyrido[2,3-d]pyrimidin-7-one compound can have a structure of Formula (II) as described in U.S. Patent Publication No. 2007/0179118 to Barvian et al., herein incorporated by reference in its entirety. In some embodiments, the pyrido [2,3-d]pyrimidine compound is 6-acetyl-8-cyclopentyl-5-methyl-2-(5-piperazin-1-yl-pyridin-2-ylamino)-8H-pyrido-[2,3-d]pyrimidin-7-one (i.e., PD 0332991) or a pharmaceutically acceptable salt thereof. See Toogood et al., *J. Med. Chem.*, 2005, 48, 2388-2406.

In some embodiments, the pyrido[2,3-d]pyrimidinone is a 2-amino-6-cyano-pyrido[2,3-d]pyrimidin-4-ones. Selective CDK4/6 inhibitors comprising a 2-amino-6-cyano-pyrido[2, 3-d]pyrimidin-4-one are described, for example, by Tu et al. See Tu et al., *Bioorg. Med. Chem. Lett.*, 2006, 16, 3578-3581.

As used herein, "triaminopyrimidines" are pyrimidine compounds wherein at least three carbons in the pyrimidine ring are substituted by groups having the formula —NR$_1$R$_2$, wherein R$_1$ and R$_2$ are independently selected from the group consisting of H, alkyl, aralkyl, cycloalkyl, heterocycle, aryl, and heteroaryl. Each R$_1$ and R$_2$ alkyl, aralkyl, cycloalkyl, heterocycle, aryl, and heteroaryl groups can further be substituted by one or more hydroxyl, halo, amino, alkyl, aralkyl, cycloalkyl, heterocyclic, aryl, or heteroaryl groups. In some embodiments, at least one of the amino groups is an alkylamino group having the structure —NHR, wherein R is $C_1$-$C_6$ alkyl. In some embodiments, at least one amino group is a cycloalkylamino group or a hydroxyl-substituted cycloalkylamino group having the formula —NHR wherein R is $C_3$-$C_7$ cycloalkyl, substituted or unsubstituted by a hydroxyl group. In some embodiments, at least one amino group is a heteroaryl-substituted aminoalkyl group, wherein the heteroaryl group can be further substituted with an aryl group substituent.

Aryl[a]pyrrolo[3,4-d]carbazoles include, but are not limited to napthyl[a]pyrrolo[3,4-c]carbazoles, indolo[a]pyrrolo [3,4-c]carbazoles, quinolinyl[a]pyrrolo[3,4-c]carbazoles, and isoquinolinyl[a]pyrrolo[3,4-c]carbazoles. See e.g., Engler et al., *Bioorg. Med. Chem. Lett.*, 2003, 13, 2261-2267; Sanchez-Martinez et al., *Bioorg. Med. Chem. Lett.*, 2003, 13, 3835-3839; Sanchez-Martinez et al., *Bioorg. Med. Chem. Lett.*, 2003, 13, 3841-3846; Zhu et al., *Bioorg. Med. Chem. Lett.*, 2003, 13, 1231-1235; and Zhu et al., *J. Med Chem.*, 2003, 46, 2027-2030. Suitable aryl[a]pyrrolo[3,4-d] carbazoles are also disclosed in U.S. Patent Publication Nos. 2003/0229026 and 2004/0048915.

Nitrogen-containing heteroaryl-substituted ureas are compounds comprising a urea moiety wherein one of the urea nitrogen atoms is substituted by a nitrogen-containing heteroaryl group. Nitrogen-containing heteroaryl groups include, but are not limited to, five to ten membered aryl groups including at least one nitrogen atom. Thus, nitrogen-containing heteroaryl groups include, for example, pyridine, pyrrole, indole, carbazole, imidazole, thiazole, isoxazole, pyrazole, isothiazole, pyrazine, triazole, tetrazole, pyrimidine, pyridazine, purine, quinoline, isoquinoline, quinoxaline, cinnoline, quinazoline, benzimidazole, phthalimide and the like. In some embodiments, the nitrogen-containing heteroaryl group can be substituted by one or more alkyl, cycloalkyl, heterocyclic, aralkyl, aryl, heteroaryl, hydroxyl, halo, carbonyl, carboxyl, nitro, cyano, alkoxyl, or amino group. In some embodiments, the nitrogen-containing heteroaryl substituted urea is a pyrazole-3-yl urea. The pyrazole can be further substituted by a cycloalkyl or heterocyclic group. In some embodiments, the pyrazol-3-yl urea is:

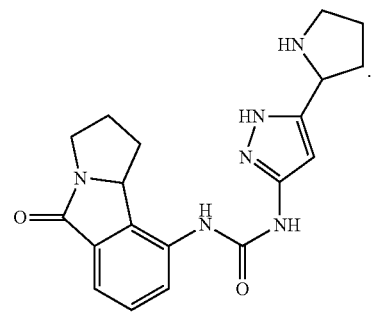 [SMILES: O=C(Nc1cc(C2CCCN2)[nH]n1)Nc1cccc2c1C1CCCN1C2=O]

See Ikuta, et al., *J. Biol. Chem.*, 2001, 276, 27548-27554. Additional ureas that can be used according to the presently disclosed subject matter include the biaryl urea compounds of Formula (I) described in U.S. Patent Publication No. 2007/0027147. See also, Honma et al., *J. Med. Chem.*, 2001, 44, 4615-4627; and Honma et al., *J. Med. Chem.*, 2001, 44, 4628-4640.

Suitable 5-pyrimidinyl-2-aminothiazole CDK4/6 inhibitors are described by Shimamura et al. See Shimamura et al., *Bioorg. Med. Chem. Lett.*, 2006, 16, 3751-3754. In some embodiments, the 5-pyrimidinyl-2-aminothiazole has the structure:

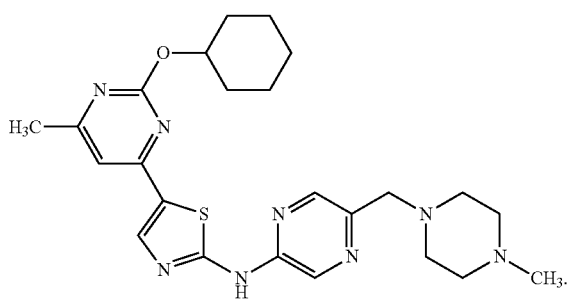 [SMILES: Cc1cc(-c2cnc(Nc3cnc(CN4CCN(C)CC4)cn3)s2)nc(OC2CCCCC2)n1]

Useful benzothiadiazine and acridinethiones compounds include those, for example, disclosed by Kubo et al. See Kubo et al., *Clin. Cancer Res.* 1999, 5, 4279-4286 and in U.S. Patent Publication No. 2004/0006074, herein incorporated by reference in their entirety. In some embodiments, the benzothiadiazine is substituted by one or more halo, haloaryl, or alkyl group. In some embodiments, the benzothiadiazine is selected from the group consisting of 4-(4-fluorobenzylamino)-1,2,3-benzothiadiazine-1,1-dioxide, 3-chloro-4-methyl-4H-benzo[e][1,2,4]thiadiazine-1,1-dioxide, and 3-chloro-4-ethyl-4H-benzo[e][1,2,4]thiadiazine-1,1-dioxide. In some embodiments, the acridinethione is substituted by one or more amino or alkoxy group. In some embodiments, the acridinethione is selected from the group consisting of 3-amino-10H-acridone-9-thione (3ATA), 9(10H)-acridinethione, 1,4-dimethoxy-10H-acridine-9-thione, and 2,2'-diphenyldiamine-bis-[N,N'-[3-amido-N-methylamino)-10H-acridine-9-thione]].

In some embodiments, the subject of the presently disclosed methods will be a subject who has been exposed to, is being exposed to, or is scheduled to be exposed to, ischemia.

Generally, CDK4/6 inhibitor compound can be administered to the subject during the time period ranging from 24 to 20 hours prior to exposure to ischemia until 24 to 48 hours following exposure. However, this time period can be extended to time earlier that 24 hour prior to exposure to the ischemia if desired. Further, the time period can be extended longer than 24 hours to 48 hours following exposure to ischemia so long as later administration of the CDK4/6 inhibitor leads to at least some protective effect.

In some embodiments, the CDK4/6 inhibitor can be administered to the subject at a time period prior to the ischemia, so that plasma levels of the CDK4/6 inhibitor are peaking at the time of administration of the ischemic event.

If desired, multiple doses of the CDK4/6 inhibitor compound can be administered to the subject. Alternatively, the subject can be given a single dose of the CDK4/6 inhibitor.

In some embodiments, the presently disclosed subject matter is related to the ability of CDK4/6 inhibitors (e.g., selective CDK4/6 inhibitors) to protect cells or tissues from ischemic damage and/or related events. Thus, in some embodiments, the presently disclosed subject matter provides a method of mitigating injury in a cell or tissue, such as a kidney, gut, heart, liver, brain, thyroid, skin, intestinal mucosa, auditory system, lung, bladder, ovary, uterus, testicle, adrenal, gallbladder, pancreas, pancreatic islet, stomach, blood vessel, or muscle cell or tissue, in a subject in need of treatment thereof prior to or following exposure of the cell or tissue to ischemia and/or a related event, wherein the method comprises administering to the subject a pharmaceutically effective amount of a compound that inhibits CDK4/6. In some embodiments, the cell or tissue is characterized by proliferation after injury that is CDK4/6 dependent, and in some embodiments the injury is ischemia-related. In some embodiments the cell or tissue is a kidney (i.e., renal) cell or tissue.

The compound that inhibits CDK4/6 can be administered at any suitable time prior to, during, or after exposure of the subject to the ischemia and/or related event. In some embodiments, the CDK4/6 inhibitor is administered to the subject between about 24 and about 48 hours (e.g., about 24, 25, 26, 27, 28, 29, 30, 31, 32, 33, 34, 35, 36, 37, 38, 39, 40, 41, 42, 43, 44, 45, 46, 47, or 48 hours) after exposure of the subject to the ischemia and/or related event. In some embodiments, the CDK4/6 inhibitor is administered to the subject prior to (e.g., 1, 2, 3, 4, 5, 6, 7, 8, 9, 10, 11, 12, 13, 14, 15, 16, 17, 18, 19, 20, 21, 22, 23, or 24 hours) prior to exposure of the subject to the ischemia and/or related event.

In some embodiments, the compound that inhibits CDK4/6 is a selective CDK4/6 inhibitor. In some embodiments, the selective CDK4/6 inhibitor has an $IC_{50}$ for CDK4 or CKD6 that is at least 2, 5, 10, 100, or 1000 times lower than the compound's $IC_{50}$s for other CDKs. In some embodiments, the selective CDK4/6 inhibitor is a poor inhibitor (e.g., has an $IC_{50}$ of >1 µM) of cyclin dependent kinases (e.g., CDK1) other than CDK4 and/or CDK6.

In some embodiments, the ischemia-inducing event is cardiac surgery (e.g., bypass surgery) or another surgery associated with hypotensive episodes. In some embodiments, the ischemia-inducing episode is renal allograft harvesting (e.g., cadaveric renal allograft harvesting) with cold-ischemia induced during transportation and/or storage of the kidney in the absence of blood flow. In some embodiments, the ischemia-inducing event is the administration of a radio-contrast agent. In some embodiments, the radio-contrast agent is used for CT scans, pylorograms, or artiography. In some embodiments, the radio-contrast agent is an iodine-containing radio-contrast agent. In some embodiments, the ischemia-inducing event is trauma associated with a period of hypovolemia (e.g., due to bleeding or dehydration) and/or hypotension.

In some embodiments, the ischemia-inducing event is administration of a medicine or agent that decreases blood flow (e.g., renal blood flow), such as, but not limited to, aspirin, ibuprofen, tacrolimus, and/or cyclosporine. In some embodiments, the ischemia-inducing event is acute tissue ischemia or infarction, such as, but not limited to, that caused by arterial embolus or in situ arterial or venous thrombosis. In some embodiments, the ischemia-inducing event is torsion of a volvulus or other transient anatomic disruption of organ blood flow.

III. Active Compounds, Salts and Formulations

As used herein, the term "active compound" refers to a CDK 4/6 inhibitor compound, or a prodrug (such as but not limited to various esters and other derivatives that can form the CDK4/6 inhibitor in vitro or in vivo), solvate (such as but not limited to a hydrate) and/or pharmaceutically acceptable salt thereof. In some embodiments, the "active compound" is a selective CDK4/6 inhibitor compound, prodrug, solvate, and/or pharmaceutically acceptable salt thereof. The active compound can be administered to the subject through any suitable approach. The amount and timing of active compound administered can, of course, be dependent on the subject being treated, on the nature of ischemia and/or a related event to which the subject has been, is being, or is anticipated of being exposed to, on the manner of administration, on the pharmacokinetic properties of the active compound, and on the judgment of the prescribing physician. Thus, because of subject to subject variability, the dosages given below are a guideline and the physician can titrate doses of the compound to achieve the treatment that the physician considers appropriate for the subject. In considering the degree of treatment desired, the physician can balance a variety of factors such as age and weight of the subject, presence of preexisting disease, as well as presence of other diseases. Pharmaceutical formulations can be prepared for any desired route of administration, including but not limited to oral, intravenous, intramuscular, i.p., or aerosol administration, as discussed in greater detail below. In some embodiments, the formulation can be prepared as a maintenance solution for an ex vivo organ (e.g., a kidney) or tissue intended for implantation into a transplant recipient.

The therapeutically effective dosage of any specific active compound, the use of which is within the scope of embodiments described herein, can vary somewhat from compound to compound, and subject to subject, and can depend upon the condition of the subject and the route of delivery. As a general proposition, a dosage from about 0.1 to about 200 mg/kg can have therapeutic efficacy, with all weights being calculated based upon the weight of the active compound, including the cases where a salt is employed. In some embodiments, the dosage can be the amount of compound needed to provide a serum concentration of the active compound of up to between about 1-5 µM or higher. Toxicity concerns at the higher level can restrict intravenous dosages to a lower level, such as up to about 10 mg/kg, with all weights being calculated based on the weight of the active base, including the cases where a salt is employed. A dosage from about 10 mg/kg to about 50 mg/kg can be employed for oral administration. Typically, a dosage from about 0.5 mg/kg to 5 mg/kg can be employed for intramuscular injection. In some embodiments, dosages can be from about 1 µmol/kg to about 50 µmol/kg, or, optionally, between about 22 µmol/kg and about 33 µmol/kg of the compound for intravenous or oral administration.

In accordance with the presently disclosed methods, pharmaceutically active compounds as described herein can be administered orally as a solid or as a liquid, or can be administered intramuscularly, intravenously or by inhalation as a solution, suspension, or emulsion. In some embodiments, the compounds or salts also can be administered by inhalation, intravenously, or intramuscularly as a liposomal suspension. When administered through inhalation the active compound or salt can be in the form of a plurality of solid particles or droplets having a particle size from about 0.5 to about 5 microns, and optionally from about 1 to about 2 microns.

The pharmaceutical formulations can comprise an active compound described herein or a pharmaceutically acceptable salt thereof, in any pharmaceutically acceptable carrier. If a solution is desired, water is the carrier of choice with respect to water-soluble compounds or salts. With respect to the water-soluble compounds or salts, an organic vehicle, such as glycerol, propylene glycol, polyethylene glycol, or mixtures thereof, can be suitable. In the latter instance, the organic vehicle can contain a substantial amount of water. The solution in either instance can then be sterilized in a suitable manner known to those in the art, and typically by filtration through a 0.22-micron filter. Subsequent to sterilization, the solution can be dispensed into appropriate receptacles, such as depyrogenated glass vials. The dispensing is optionally done by an aseptic method. Sterilized closures can then be placed on the vials and, if desired, the vial contents can be lyophilized.

In addition to the active compounds or their salts, the pharmaceutical formulations can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain antimicrobial preservatives. Useful antimicrobial preservatives include methylparaben, propylparaben, and benzyl alcohol. An antimicrobial preservative is typically employed when the formulation is placed in a vial designed for multi-dose use. The pharmaceutical formulations described herein can be lyophilized using techniques well known in the art.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch (e.g., potato or tapioca starch) and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules. Materials in this connection also include lactose or milk sugar as well as high molecular weight polyethylene glycols. When aqueous suspensions and/or elixirs are desired for oral administration, the compounds of the presently disclosed subject matter can be combined with various sweetening agents, flavoring agents, coloring agents, emulsifying agents and/or suspending agents, as well as such diluents as water, ethanol, propylene glycol, glycerin and various like combinations thereof.

In yet another embodiment of the subject matter described herein, there is provided an injectable, stable, sterile formulation comprising an active compound as described herein, or a salt thereof, in a unit dosage form in a sealed container. The compound or salt is provided in the form of a lyophilizate, which is capable of being reconstituted with a suitable pharmaceutically acceptable carrier to form a liquid formulation suitable for injection thereof into a subject. When the compound or salt is substantially water-insoluble, a sufficient amount of emulsifying agent, which is physiologically acceptable, can be employed in sufficient quantity to emulsify the compound or salt in an aqueous carrier. Particularly useful emulsifying agents include phosphatidyl cholines and lecithin.

Additional embodiments provided herein include liposomal formulations of the active compounds disclosed herein. The technology for forming liposomal suspensions is well known in the art. When the compound is an aqueous-soluble salt, using conventional liposome technology, the same can be incorporated into lipid vesicles. In such an instance, due to the water solubility of the active compound, the active compound can be substantially entrained within the hydrophilic center or core of the liposomes. The lipid layer employed can be of any conventional composition and can either contain cholesterol or can be cholesterol-free. When the active compound of interest is water-insoluble, again employing conventional liposome formation technology, the salt can be substantially entrained within the hydrophobic lipid bilayer that forms the structure of the liposome. In either instance, the liposomes that are produced can be reduced in size, as through the use of standard sonication and homogenization techniques. The liposomal formulations comprising the active compounds disclosed herein can be lyophilized to produce a lyophilizate, which can be reconstituted with a pharmaceutically acceptable carrier, such as water, to regenerate a liposomal suspension.

Pharmaceutical formulations also are provided which are suitable for administration as an aerosol by inhalation. These formulations comprise a solution or suspension of a desired compound described herein or a salt thereof, or a plurality of solid particles of the compound or salt. The desired formulation can be placed in a small chamber and nebulized. Nebulization can be accomplished by compressed air or by ultrasonic energy to form a plurality of liquid droplets or solid particles comprising the compounds or salts. The liquid droplets or solid particles should have a particle size in the range of about 0.5 to about 10 microns, and optionally from about 0.5 to about 5 microns. The solid particles can be obtained by processing the solid compound or a salt thereof, in any appropriate manner known in the art, such as by micronization. Optionally, the size of the solid particles or droplets can be from about 1 to about 2 microns. In this respect, commercial nebulizers are available to achieve this purpose. The compounds can be administered via an aerosol suspension of respirable particles in a manner set forth in U.S. Pat. No. 5,628,984, the disclosure of which is incorporated herein by reference in its entirety.

When the pharmaceutical formulation suitable for administration as an aerosol is in the form of a liquid, the formulation can comprise a water-soluble active compound in a carrier that comprises water. A surfactant can be present, which lowers the surface tension of the formulation sufficiently to result in the formation of droplets within the desired size range when subjected to nebulization.

As indicated, both water-soluble and water-insoluble active compounds are provided. As used herein, the term "water-soluble" is meant to define any composition that is soluble in water in an amount of about 50 mg/mL, or greater. Also, as used herein, the term "water-insoluble" is meant to define any composition that has a solubility in water of less than about 20 mg/mL. In some embodiments, water-soluble compounds or salts can be desirable whereas in other embodiments water-insoluble compounds or salts likewise can be desirable.

The term "pharmaceutically acceptable salts" as used herein refers to those salts which are, within the scope of sound medical judgment, suitable for use in contact with subjects (e.g., human subjects) without undue toxicity, irritation, allergic response, and the like, commensurate with a reasonable benefit/risk ratio, and effective for their intended use, as well as the zwitterionic forms, where possible, of the compounds of the presently disclosed subject matter.

Thus, the term "salts" refers to the relatively non-toxic, inorganic and organic acid addition salts of compounds of the presently disclosed subject matter. These salts can be prepared in situ during the final isolation and purification of the compounds or by separately reacting the purified compound in its free base form with a suitable organic or inorganic acid and isolating the salt thus formed. In so far as the compounds of the presently disclosed subject matter are basic compounds, they are all capable of forming a wide variety of different salts with various inorganic and organic acids. Although such salts must be pharmaceutically acceptable for administration to animals, it is often desirable in practice to initially isolate the base compound from the reaction mixture as a pharmaceutically unacceptable salt and then simply convert to the free base compound by treatment with an alkaline reagent and thereafter convert the free base to a pharmaceutically acceptable acid addition salt. The acid addition salts of the basic compounds are prepared by contacting the free base form with a sufficient amount of the desired acid to produce the salt in the conventional manner. The free base form can be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the presently disclosed subject matter.

Pharmaceutically acceptable base addition salts are formed with metals or amines, such as alkali and alkaline earth metal hydroxides, or of organic amines. Examples of metals used as cations, include, but are not limited to, sodium, potassium, magnesium, calcium, and the like. Examples of suitable amines include, but are not limited to, N,N'-dibenzylethylenediamine, chloroprocaine, choline, diethanolamine, ethylenediamine, N-methylglucamine, and procaine.

The base addition salts of acidic compounds are prepared by contacting the free acid form with a sufficient amount of the desired base to produce the salt in the conventional manner. The free acid form can be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes of the presently disclosed subject matter.

Salts can be prepared from inorganic acids sulfate, pyrosulfate, bisulfate, sulfite, bisulfite, nitrate, phosphate, monohydrogenphosphate, dihydrogenphosphate, metaphosphate, pyrophosphate, chloride, bromide, iodide such as hydrochloric, nitric, phosphoric, sulfuric, hydrobromic, hydriodic, phosphorus, and the like. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, laurylsulphonate and isethionate salts, and the like. Salts can also be prepared from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. and the like. Representative salts include acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Pharmaceutically acceptable salts can include cations based on the alkali and alkaline earth metals, such as sodium, lithium, potassium, calcium, magnesium and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. Also contemplated are the salts of amino acids such as arginate, gluconate, galacturonate, and the like. See, for example, Berge et al., *J. Pharm. Sci.,* 1977, 66, 1-19, which is incorporated herein by reference.

EXAMPLES

The following Examples provide illustrative embodiments and are not intended to limit the scope of the presently disclosed subject matter in any way. In light of the present disclosure and the general level of skill in the art, those of skill can appreciate that the following Examples are intended to be exemplary only and that numerous changes, modifications, and alterations can be employed without departing from the scope of the presently disclosed subject matter.

The practice of the presently disclosed subject matter can employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, Biochemistry (Worth Publishers, Inc., current edition); Sambrook et al., *Molecular Cloning: A Laboratory Manual* (2nd Edition, 1989); *Methods in Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg, *Advanced Organic Chemistry* 3rd Ed. (Plenum Press) Vols A and B (1992). PCT Publication Nos. WO 2010/051127, WO 2010/039997; and WO 2010/132725 are also herein incorporated by reference in its entirety.

Example 1

Synthesis of PD

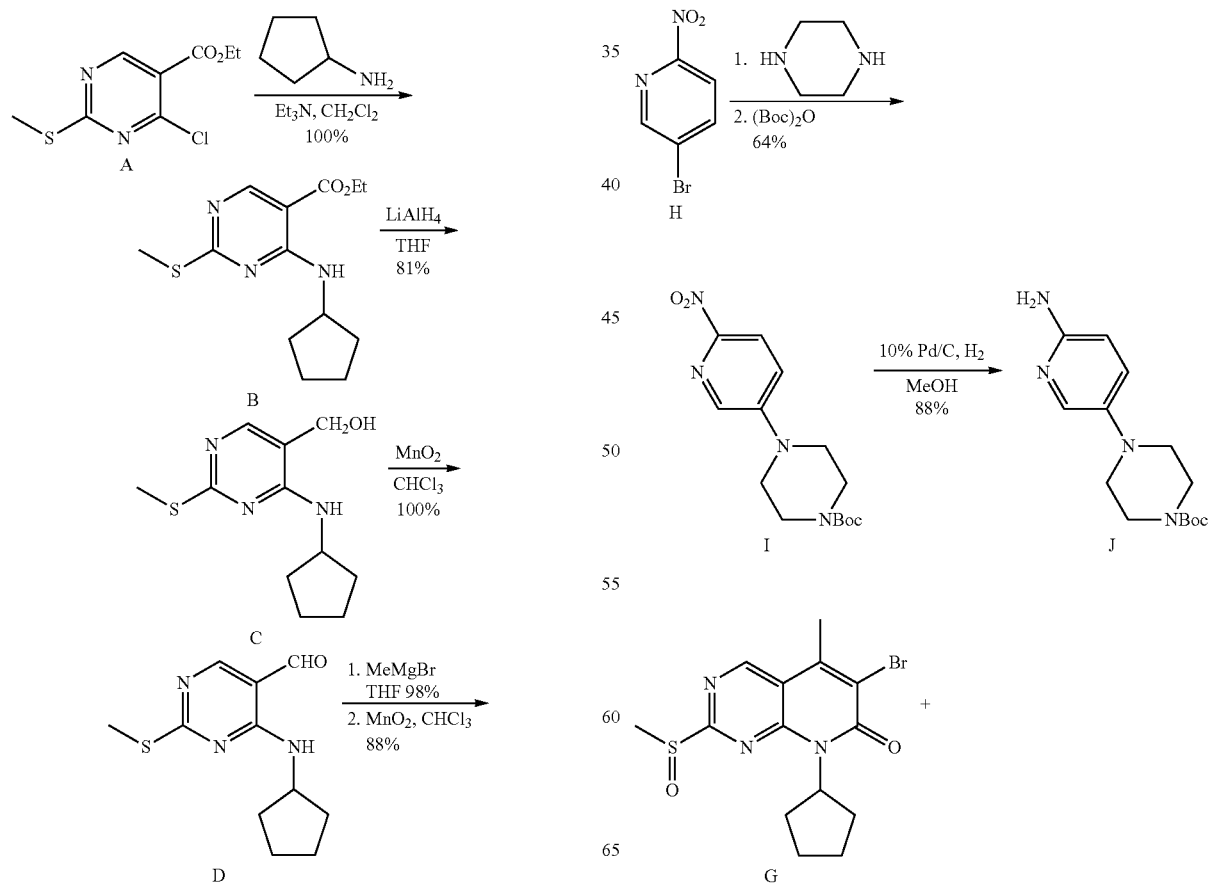

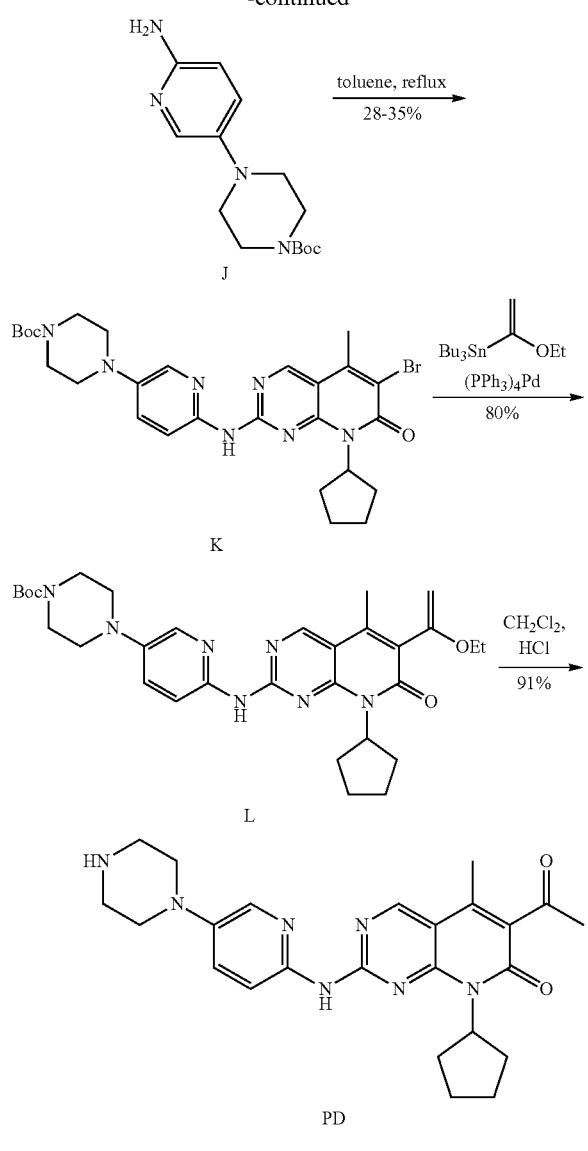

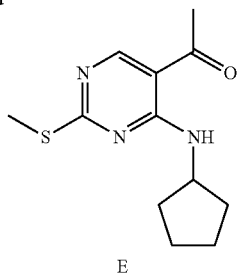

Compound D (40 g, 169 mmol) was dissolved in anhydrous THF (800 mL) under nitrogen and the solution was cooled in ice bath, to which MeMgBr was added slowly (160 mL, 480 mmol, 3 M in ether) and stirred for 1 h. The reaction was quenched with saturated aqueous NH₄Cl the partitioned between water and EtOAc. The organic layer was separated and the aqueous layer was extracted with EtOAc. The combined organic were washed with brine and dried over MgSO₄. Concentration gave an intermediate product as an oil (41.9 g, 98%).

The above intermediate (40 g, 158 mmol) was dissolved in dry CHCl₃ (700 mL). MnO₂(96 g, 1.11 mol) was added and the mixture was heated to reflux with stirring for 18 h and another MnO₂ (34 g, 395 mmol) was added and continue to reflux for 4 h. The solid was filtrated through a Celite pad and washed with CHCl₃. The filtrate was concentrated to give a yellow solid compound E (35 g, 88%), Mp: 75.8-76.6° C.

Conversion of Compound F to Compound G:

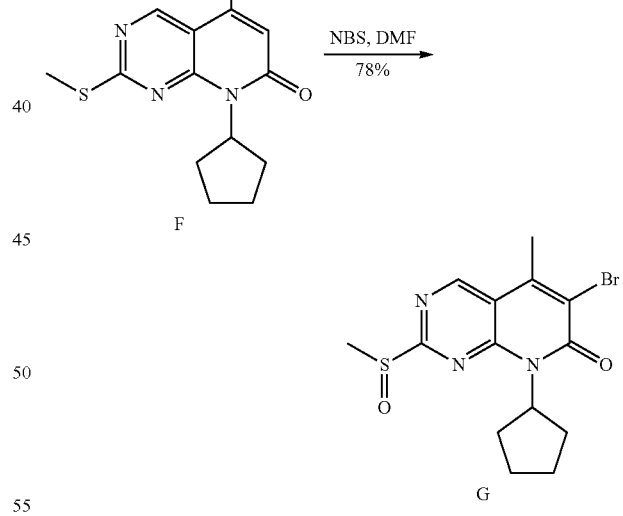

PD was synthesized as shown above in Scheme 1. Reactions shown in Scheme 1 generally followed previously reported procedures (see VandelWel et al., *J. Med. Chem.*, 48, 2371-2387 (2005); and Toogood et al., *J. Med. Chem.*, 48, 2388-2406 (2005)), with the exceptions of the reaction converting compound D to compound E and the reaction converting compound F to compound G.

Conversion of Compound D to Compound E:

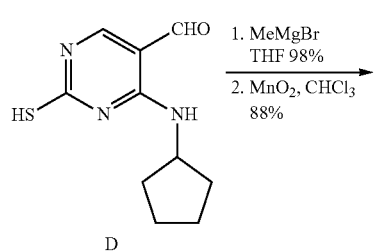

Compound F (5 g, 18.2 mmol) was dissolved in anhydrous DMF (150 mL) and NBS (11.3 g, 63.6 mmol) was added. The reaction mixture was stirred at r.t. for 3.5 h and then poured into H₂O (500 mL), the precipitate was filtered and washed with H₂O. The solid recrystallized from EtOH to give compound G as a white solid (5.42 g, 80.7%), mp: 210.6-211.3° C.

Characterization Data for PD:

LC-MS: 448.5 (ESI, M+H). Purity: ~99%

¹H NMR (300 MHz, D₂O): 9.00 (s, 1H), 8.12 (dd, J=9.3 Hz, 2.1 Hz, 1H), 7.81 (d, J=2.4 Hz, 1H), 7.46 (d, J=9.6 Hz,

1H), 5.80-5.74 (m, 1H), 3.57-3.48 (m, 8H), 2.48 (s, 3H), 2.37 (s, 3H), 2.13-1.94 (m, 6H), 1.73-1.71 (m, 2H).

$^{13}$C NMR (75 MHz, D$_2$O): 203.6, 159.0, 153.5, 153.3, 152.2, 139.9, 139.4, 139.2, 133.1, 129.0, 118.7, 113.8, 107.4, 51.8, 42.2, 40.0, 28.0, 25.2, 22.6, 10.8.

Example 2

Protection of Non-Hematologic Tissues and Cells by CDK4/6 Inhibition

Figure 1A:
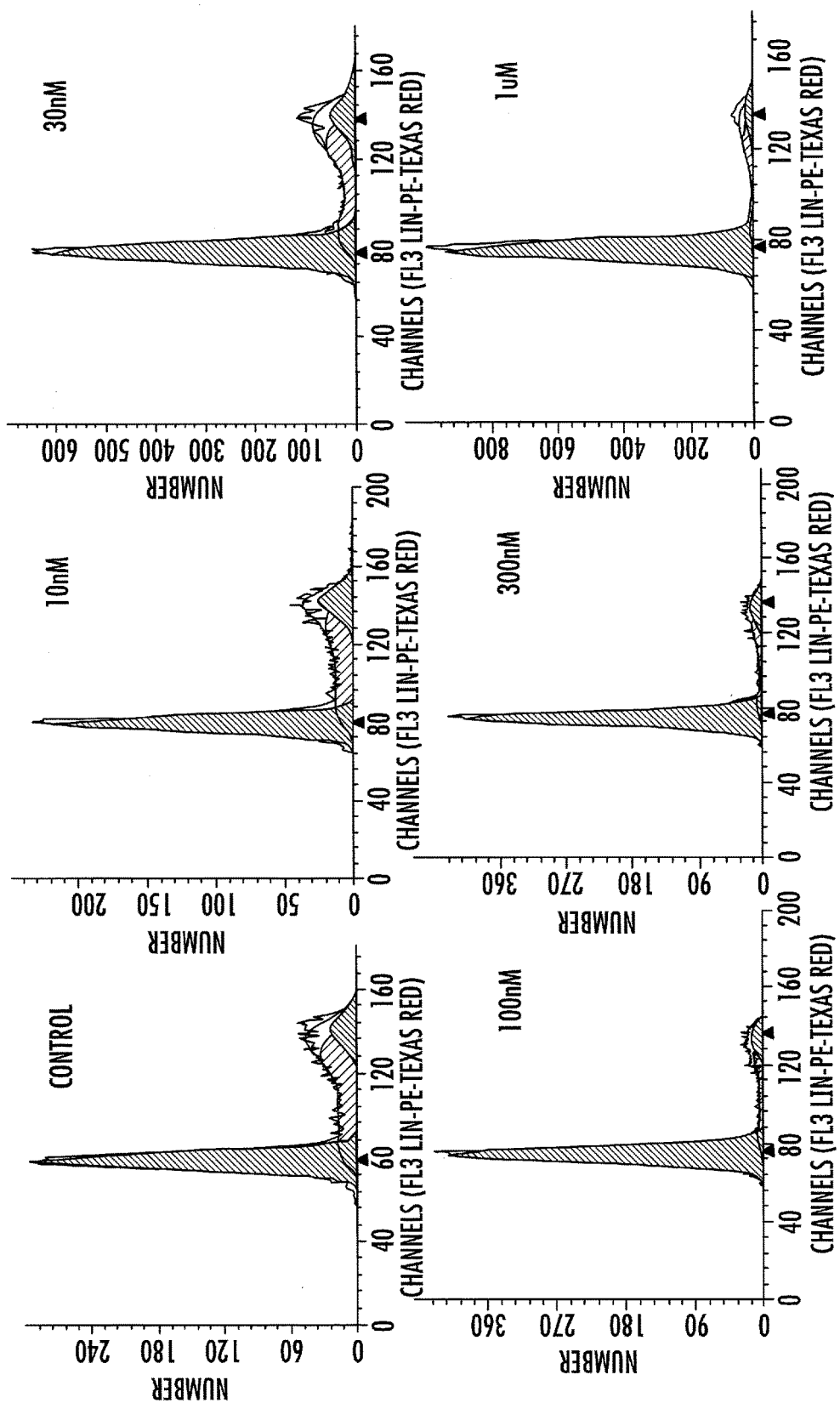
FIG. 1A is a set of histograms showing that CDK4/6 inhibition induces a $G_1$ arrest in primary human renal proximal tubule epithelial cells. Representative histograms of cell cycle analysis of primary human renal proximal tubule epithelial cells treated with varying concentrations (0 nM, 10 nM, 30 nM, 100 nM, 300 nM, or 1 μM) of 6-acetyl-8-cyclopentyl-5-methyl-2-(5-piperazin-1-yl-pyridin-2-ylamino)-8H-pyrido-[2,3-d]pyrimidin-7-one (PD0332991) for 16 hours. Cells were harvested, fixed, stained, and analyzed by flow cytometry. Data was fitted using Mod-Fit™ software from Verity (Verity Software House, Topsham, Me., United States of America). Increasing concentrations of CDK4/6 inhibitor produce a "clean" G1-arrest without evidence of cytotoxicity.
Figure 1B:
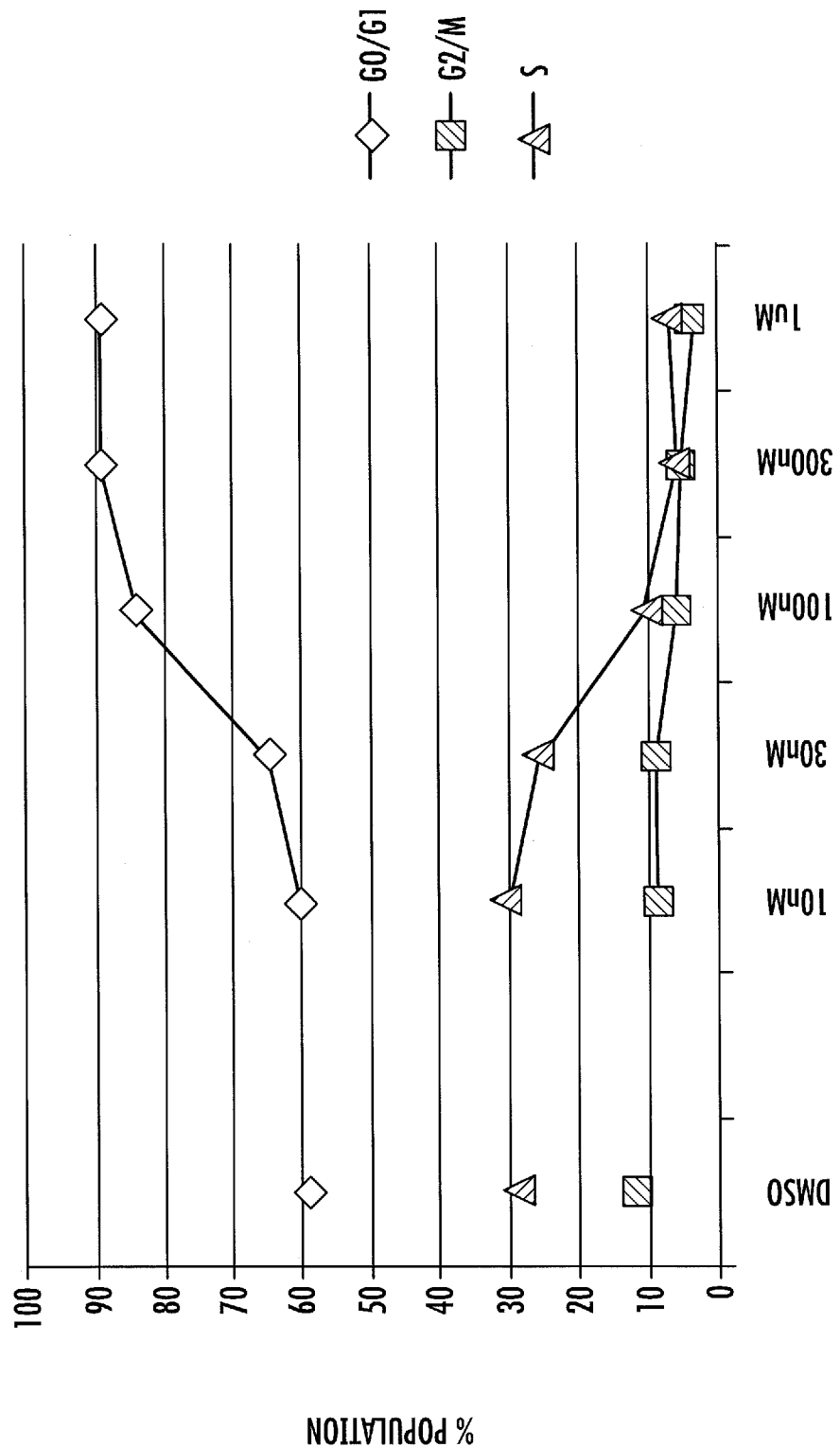
FIG. 1B is a line graph showing that CDK4/6 inhibition induces a $G_1$ arrest in primary human renal proximal tubule epithelial cells. Cell cycle analysis of primary human renal proximal tubule epithelial cells treated with varying concentrations (0 nM, 10 nM, 30 nM, 100 nM, 300 nM, or 1 μM) of 6-acetyl-8-cyclopentyl-5-methyl-2-(5-piperazin-1-yl-pyridin-2-ylamino)-8H-pyrido-[2,3-d]pyrimidin-7-one (PD0332991) for 16 hours. Cells were harvested, fixed, stained, and analyzed by flow cytometry. Data was fitted using Mod-Fit™ software from Verity (Verity Software House, Topsham, Me., United States of America). Corresponding % of cells in G1 (diamonds), G2/M (squares) and S (triangles) are shown on the graph.

Use of a potent and selective CDK4/6 inhibitor, such as PD0332991 (synthesized as described in Example 1), induces a G1 arrest in normal human primary renal proximal tubule epithelial cells. See FIGS. 1A and 1B. A dose dependent increase in the G0/G1 fraction of the cell cycle was observed with a consummate decrease in both G2/M and S-phase fractions. In doing so, the cells enter pharmacologic quiescence and are held in this state until they are released from this arrest.

Normal human primary renal proximal tubule epithelial cells were plated and exposed 24 hours later to PD0332991 at concentrations of 0, 10 nM, 30 nM, 100 nM, 300 nM or 1 µM. Sixteen hours post treatment; cells were harvested by standard methods, fixed in ice-cold methanol until time for DNA staining. Samples were processed and the DNA was stained with propidium iodide (PI) solution and analyzed by flow cytometry. FCS files from flow cytometer were further analyzed using cell cycle analysis software ModFit™ from Verity (Verity Software House, Topsham, Me., United States of America), where cell cycle fractions were calculated as a percentage of the whole population.

Figure 2:
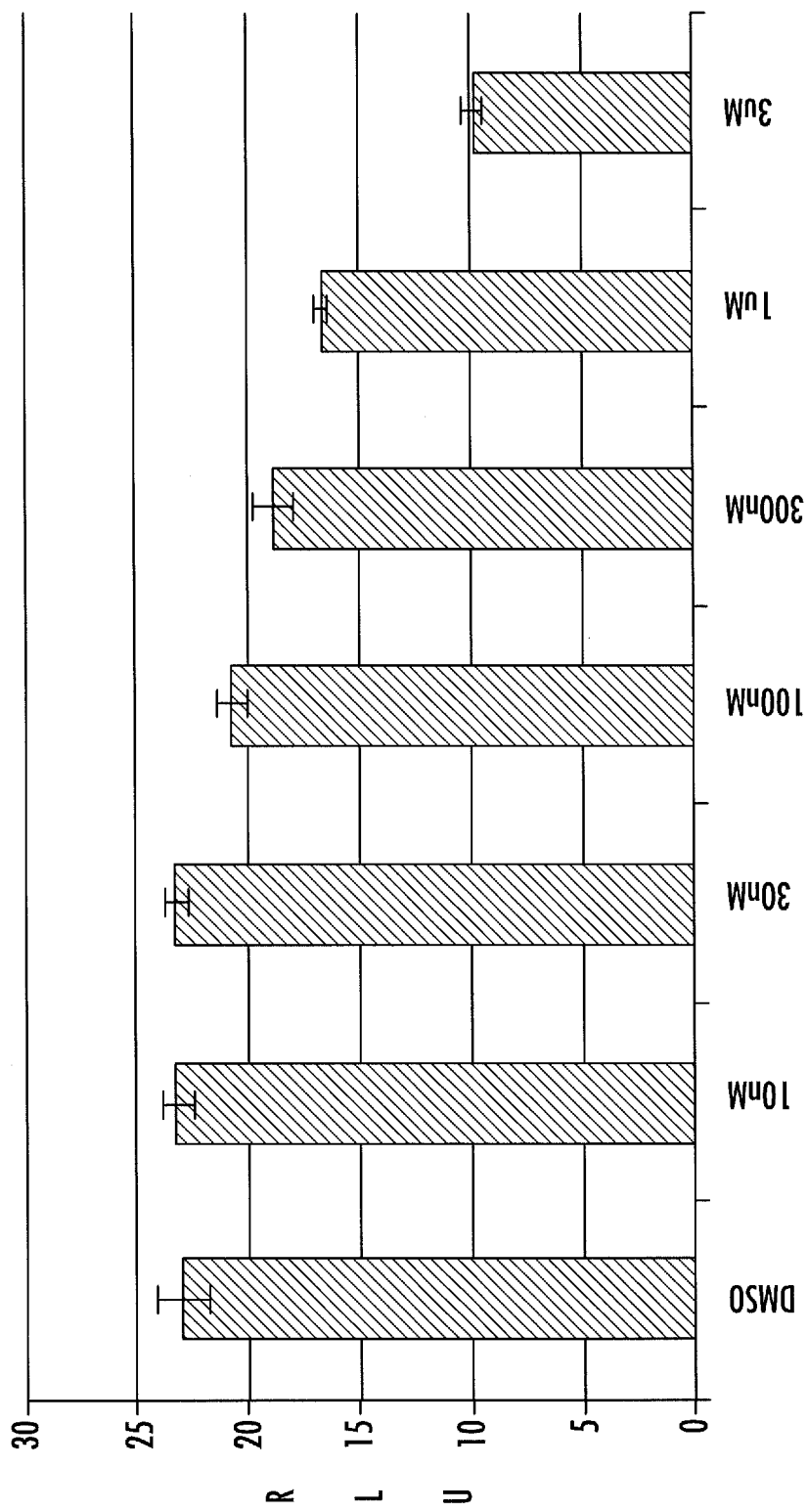
FIG. 2 is a bar graph showing that CDK4/6 inhibition blocks proliferation of primary human renal proximal tubule epithelial cells. Cells were treated with varying concentrations (0 nM, 10 nM, 30 nM, 100 nM, 300 nM, or 1 μM) of 6-acetyl-8-cyclopentyl-5-methyl-2-(5-piperazin-1-yl-pyridin-2-ylamino)-8H-pyrido-[2,3-d]pyrimidin-7-one (PD0332991) for 72 hours. Following incubation, cell proliferation was quantified using CellTiter-Glo® (Promega, Madison, Wis., United States of America). Data represent the mean of four replicates (relative light units, RLU)+/−standard deviation.

Inhibition of CDK4/6 blocks the proliferation of normal human primary renal proximal tubule epithelial cells. These cells were seeded at an appropriate density in 96 well plates and incubated for 24 hours at 37° C. in a humidified incubator at 5% CO$_2$. Cells were then exposed to a potent and selective CDK4/6 inhibitor, in this case PD0332991, across a broad dose range 24 hours later. The dose range explored is 0, 10 nM, 30 nM, 100 nM, 300 nM, 1 µM or 3 µM PD0332991. Seventy-two hours post exposure, the CDK4/6 inhibited cells were treated with CellTiter-Glo® (Promega, Madison, Wis., United States of America) using manufacturer's specifications. The plate was read in luminometer at 1 second/well. Results were placed in Microsoft Excel and analyzed. In FIG. 2, a clear dose dependent inhibition of cell proliferation is obtained in the presence of this inhibitor when compared to DMSO control by 72 hours post treatment. This result, in conjunction with FIGS. 1A and 1B demonstrates that CDK4/6 dependent non-hematologic cells can enter pharmacologic quiescence and are thusly inhibited from proliferating.

Example 3

Methods for Treatment of Mice with PD0332991, IRI and BrdU Incorporation into Renal Epithelial Cells Compounds:
PD0332991 was synthesized as described in Example 1.
Drug Preparation and Dosing:
PD0332991 was dissolved in 50 mM sodium lactate buffer (pH 4.0) to a final concentration of 15 mg/mL. Mice were treated with a 150 mg/kg dose of PD0332991, or vehicle, 1 hour prior to ischemia reperfusion surgery by oral gavage.

Dosing Schedules:
Kidney cell proliferation following ischemia reperfusion injury (IRI) was monitored (based on BrdU incorporation in renal epithelial cells) following a one time, pre-IRI PD0332991 or vehicle (sodium lactate buffer) dosing as shown in FIG. 3A and following a two time (once pre-IRI and once post-IRI) PD0332991 or vehicle dosing as shown in FIG. 3B. BrdU (100 mg/kg) was injected i.p. either 21 hours following IRI or both 21 hours and 45 hours after IRI. Mice were sacrificed 3 hours following the final BrdU dose. BrdU positive (BrdU(+)) cells were quantified visually by counting the number of BrdU(+) cells in a field of kidney epithelial cells under magnification.

Bilateral Ischemia Reperfusion Injury:
8 week old male mice were anesthetized with pentobarbital sodium (60 mg/kg body weight, intraperitoneally) prior to surgery. Body temperatures were controlled at 36.5° C.-37.5° C. throughout the procedure. Bilateral flank incisions into the peritoneum allowed access to both kidneys. Kidneys were exposed and ischemia was induced by simultaneously clamping the renal pedicle of both kidneys with nontraumatic microaneurysm clamps (Roboz, Rockville, Md.). Clamped kidneys were placed back into the peritoneal cavity for 28 minutes, and clamps were then removed resulting in reperfusion injury. The flank incisions were closed with wound clips and the mice were allowed to recover in their home cages.

Summary:
Kidneys subjected to IRI and dosed with PD0332991 one time according to the dosing schedule of FIG. 3A showed significantly less BrdU(+) cells than injured kidneys from mice treated with vehicle 24 hours after injury. See FIG. 4A. Mice receiving two doses of PD0332991 also displayed less BrdU incorporation than mice receiving two doses of vehicle 48 hours after injury. See FIG. 4B. Kidney cells from mice that had not been subjected to IRI showed little BrdU incorporation. See FIGS. 4A and 4B.

Example 4

Methods for Treatment of Mice with PD0332991, Bilateral IRI, and Serum Creatinine Measurements Compounds:
PD0332991 was synthesized as described in Example 1.
Drug Preparation and Dosing:
PD0332991 was dissolved in 50 mM sodium lactate buffer (pH 4.0) to a final concentration of 15 mg/mL. Mice were treated with a 150 mg/kg dose of PD0332991, or vehicle, 1 hour prior to ischemia reperfusion surgery by oral gavage.

Bilateral Ischemia Reperfusion Injury:
8 week old male mice were anesthetized with pentobarbital sodium (60 mg/kg body weight, intraperitoneally) prior to surgery. Body temperatures were controlled at 36.5° C.-37.5° C. throughout the procedure. Bilateral flank incisions into the peritoneum allowed access to both kidneys. Kidneys were exposed and ischemia was induced by simultaneously clamping the renal pedicle of both kidneys with nontraumatic microaneurysm clamps (Roboz, Rockville, Md.). Clamped kidneys were placed back into the peritoneal cavity for 28 minutes, and clamps were then removed resulting in reperfusion injury. The flank incisions were closed with wound clips and the mice were allowed to recover in their home cages.

Serum Creatinine Measurements:

24 hours after surgery, tail vein blood was collected in heparinized micro-hematocrit capillary tubes (Fisher Scientific, Pittsburgh, Pa., United States of America, Cat. #22-362-566) and centrifuged for 15 minutes at 5000 revolutions per minute (RPM). The supernatant was retained as serum. Serum creatinine was measured by the Beckman Creatinine Analyzer 2, which utilizes a 10 mM picric acid solution mixed with a buffer containing 10 mM sodium borate, 240 mM sodium hydroxide, and 10 mM sodium dodecyl sulfate (SDS). Serum creatinine is measured against a creatinine standard and recorded as milligrams per deciliter.

Summary:

One hour prior to bilateral ischemic reperfusion injury, mice were treated with a 50 mM sodium lactate buffer solution or 150 mg/kg dose of PD0332991. Twenty-four hours after surgery blood was collected via the tail vein into heparinized micro-hematocrit capillary tubes. Serum was then extracted from the collected blood, and serum creatinine measurements were taken on the Beckman Creatnine Analyzer 2 per manufacturer's instructions. Results show that the average serum creatinine measurement for the group of 8 mice receiving vehicle treatment is 2.27 mg/dL±0.0732, while the 9 mice receiving PD0332991 had an average creatinine measurement of 1.74 mg/dL±0.143. Comparison between the drug treated group and vehicle treated group by unpaired t-test results in a significant difference with a p-value of 0.0062. Baseline serum creatinine was also measured 7 days prior to the surgery, and vehicle treated and drug treated groups had similar average levels of creatinine at 0.050 mg/dL and 0.044 mg/dL, respectively. See FIG. 5.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method of mitigating injury in a cell that proliferates in response to ischemia in a subject in need of treatment, the method comprising administering to the subject a pharmaceutically effective amount of a compound that inhibits cyclin dependent kinase 4 (CDK4) and cyclin dependent kinase 6 (CDK6), wherein the compound has a 50% inhibitory concentration ($IC_{50}$) for CDK4 that is at least 6 times lower than the compound's $IC_{50}$ for cyclin dependent kinase 2 (CDK2), wherein the cell proliferation is CDK4/6 dependent, and wherein the cell that proliferates in response to ischemia is a renal cell.

2. The method of claim 1, wherein the compound is administered to the subject prior to the subject being exposed to the ischemia-inducing event.

3. The method of claim 1, wherein the compound is administered at the same time the subject is being exposed to the ischemia-inducing event.

4. The method of claim 1, wherein the compound is administered after exposure of the subject to the ischemia-inducing event.

5. The method of 4, wherein the compound is administered to the subject between about 24 and about 48 hours after exposure of the subject to the ischemia-inducing event.

6. The method of claim 1, wherein the compound is administered to the subject such that therapeutic levels are maintained until conditions inducing renal injury have been reversed.

7. The method of claim 1, wherein the compound is administered to the subject such that therapeutic levels are maintained for between 12 and 72 hours following exposure to the ischemia.

8. The method of claim 2, wherein the compound is administered to the subject such that plasma levels of the compound are peaking at the time of the ischemia.

9. The method of claim 2, wherein the compound is administered to the subject 24 to 20 hours prior to the subject being exposed to the ischemia.

10. The method of claim 1, wherein the compound has an $IC_{50}$ for CDK4 that is at least 50 times lower than the $IC_{50}$ for CDK2.

11. The method of claim 1, wherein the compound has an $IC_{50}$ for CDK4 that is at least 100 times lower than the $IC_{50}$ for CDK2.

12. The method of claim 1, wherein the compound has an $IC_{50}$ for CDK4 that is at least 1000 times lower than the $IC_{50}$ for CDK2.

13. The method of claim 1, wherein the compound is substantially free of off-target effects other than inhibition of CDK6.

14. The method of claim 1, wherein the ischemia-inducing event is cardiac surgery, or other surgery associated with hypotensive episodes.

15. The method of claim 1, wherein the ischemia-inducing event is the administration of radio-contrast agents.

16. The method of claim 1, where the ischemia-inducing event is trauma associated with a period of hypovolemia and/or hypotension.

17. The method of claim 1, where the ischemia-inducing event is administration of a medicine or agent that decreases renal blood flow.

18. The method claim 1, where the ischemia-inducing event is acute tissue ischemia or infarction as caused by arterial embolus or in situ arterial or venous thrombosis.

19. The method of claim 1, where the ischemia-inducing event is torsion of a volvulus or other transient anatomic disruption of organ blood flow.

20. The method of claim 1, where the ischemia-inducing event is kidney harvesting and/or transportation prior to implantation in a kidney transplant recipient.

21. The method of claim 1, wherein the inhibitor compound is selected from the group consisting of a pyrido[2,3-d]pyrimidine, a triaminopyrimidine, an aryl[a]pyrrolo[3,4-c]carbazole, a nitrogen-containing heteroaryl-substituted urea, a 5-pyrimidinyl-2-aminothiazole, a benzothiadiazine, and an acridinethione.

* * * * *

UNITED STATES PATENT AND TRADEMARK OFFICE
CERTIFICATE OF CORRECTION

PATENT NO. : 9,808,461 B2
APPLICATION NO. : 13/988158
DATED : November 7, 2017
INVENTOR(S) : DiRocco et al.

Page 1 of 1

It is certified that error appears in the above-identified patent and that said Letters Patent is hereby corrected as shown below:

In the Specification

At Column 1, Line 15 under the heading "GOVERNMENT INTEREST":
Please delete the following paragraph:
"The presently disclosed subject matter was made with U.S. Government support under Grant No. R43 AI084284 awarded by the National Institutes of Health. Thus, the U.S. Government has certain rights in the presently disclosed subject matter."
And replace it with the following paragraph:
--This invention was made with government support under Grant Numbers AI084284 awarded by the National Institutes of Health. The government has certain rights in the invention.--

Signed and Sealed this
Nineteenth Day of June, 2018

Andrei Iancu
*Director of the United States Patent and Trademark Office*